(12) United States Patent
Neustadt et al.

(10) Patent No.: US 7,067,655 B2
(45) Date of Patent: Jun. 27, 2006

(54) ADENOSINE A2A RECEPTOR ANTAGONISTS

(75) Inventors: Bernard R. Neustadt, West Orange, NJ (US); Neil Lindo, New Providence, NJ (US)

(73) Assignee: Schering Corporation, Kenilworth, NJ (US)

(*) Notice: Subject to any disclaimer, the term of this patent is extended or adjusted under 35 U.S.C. 154(b) by 178 days.

(21) Appl. No.: 10/912,834

(22) Filed: Aug. 6, 2004

(65) Prior Publication Data

US 2005/0026932 A1 Feb. 3, 2005

Related U.S. Application Data

(62) Division of application No. 10/448,854, filed on May 30, 2003, which is a division of application No. 09/865,071, filed on May 24, 2001, now Pat. No. 6,630,475.

(60) Provisional application No. 60/207,143, filed on May 26, 2000.

(51) Int. Cl.
C07D 417/00 (2006.01)
C07D 239/00 (2006.01)
C07D 413/00 (2006.01)
C07D 401/00 (2006.01)
C07D 403/00 (2006.01)

(52) U.S. Cl. .................... 544/115; 544/238; 544/251; 544/230

(58) Field of Classification Search ................ 544/238, 544/251, 230, 115, 61
See application file for complete search history.

(56) References Cited

U.S. PATENT DOCUMENTS 5,565,460 A 10/1996 Suzuki et al.

FOREIGN PATENT DOCUMENTS

| EP | 0 217 748 | 2/1991 |
|---|---|---|
| WO | WO 95/01356 | 1/1995 |
| WO | WO 97/05138 | 2/1997 |
| WO | WO 98/52568 | 11/1998 |

OTHER PUBLICATIONS

Baraldi et al, *J. Med. Chem.*, 39 (1996), p. 1164-1171.
Seela et al, *Helvetica Chimca Acta*, 69 (1986), p. 1602-1613.
Ungerstedt et al, *Brian Research*, 24 (1970), p. 485-493.
Ungerstedt, *Eur. J. Pharmacol.*, 5 (1968), p. 107-110.
Adami et al, *Br. J. Pharmacol.*, 126, (Mar., 1999), 283P.

Primary Examiner—Alton Pryor
(74) Attorney, Agent, or Firm—Anita W. Magatti

(57) ABSTRACT

Compounds having the structural formula I

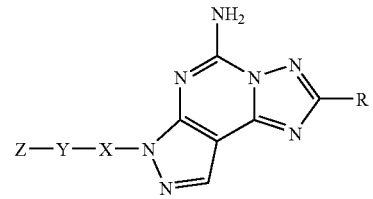

or a pharmaceutically acceptable salt thereof, wherein R is optionally substituted phenyl, cycloalkenyl, or heteroaryl;

X is alkylene or —C(O)CH$_2$—;

Y is —N(R$^2$)CH$_2$CH$_2$N(R$^3$)—, —OCH$_2$CH$_2$N(R$^2$)—, —O—, —S—, —CH$_2$S—, —(CH$_2$)$_2$—NH—, or optionally substituted

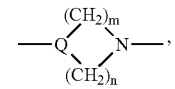

m and n are 2–3, and Q is nitrogen or optionally substituted carbon; and Z is optionally substituted phenyl, phenylalkyl or heteroaryl, diphenylmethyl, R$^6$—C(O)—, R$^6$—SO$_2$—, R$^6$—OC(O)—, R$^7$—N(R$^8$)—C(O)—, R$^7$—N(R$^8$)—C(S)—,

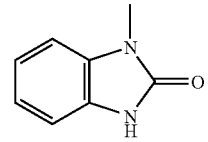

phenyl-CH(OH)—, or phenyl-C(=NOR$^2$)—; or when Q is CH, phenylamino or pyridylamino; or Z and Y together are substituted piperidinyl or substituted phenyl; and R$^2$, R$^3$, R$^6$, R$^7$, and R$^8$ are as defined in the specification are disclosed, their use in the treatment of Parkinson's disease, alone or in combination with other agents for treating Parkinson's disease, and pharmaceutical compositions comprising them; also disclosed are a processes for preparing intermediates useful for preparing compounds of formula I.

3 Claims, No Drawings

ADENOSINE A2A RECEPTOR ANTAGONISTS

CROSS REFERENCE TO RELATED APPLICATION

This application is a divisional of U.S. Ser. No. 10/448,854, filed May 30, 2003, which was a divisional of U.S. Ser. No. 09/865,071 filed May 24, 2001, now U.S. Pat. No. 6,630,475, which claimed the benefit of U.S. Provisional Application Ser. No. 60/207,143, filed May 26, 2000.

BACKGROUND

The present invention relates to substituted 5-amino-pyrazolo-[4,3-e]-1,2,4-triazolo[1,5-c]pyrimidine adenosine $A_{2a}$ receptor antagonists, the use of said compounds in the treatment of central nervous system diseases, in particular Parkinson's disease, and to pharmaceutical compositions comprising said compounds. The invention also relates to a process for preparing 5-amino-2-(substituted)pyrazolo[4,3-e]-1,2,4-triazolo-[1,5-c]pyrimidines, intermediates useful in preparing the claimed compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists with different substitution at the 7-position have been disclosed previously, for example in WO 95/01356; U.S. Pat. No. 5,565,460; WO 97/05138; and WO 98/52568.

SUMMARY OF THE INVENTION

The present invention relates to compounds having the structural formula I

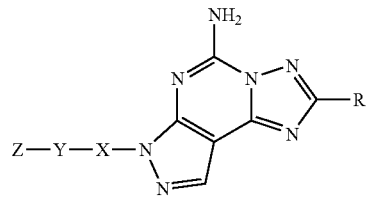

or a pharmaceutically acceptable salt thereof, wherein

R is $R^1$-furanyl, $R^1$-thienyl, $R^1$-pyridyl, $R^1$-pyridyl N-oxide, $R^1$-oxazolyl, $R^{10}$-phenyl, $R^1$-pyrrolyl or $C_4$–$C_6$ cycloalkenyl;

X is $C_2$–$C_6$ alkylene or —C(O)CH$_2$—;

Y is —N(R$^2$)CH$_2$CH$_2$N(R$^3$)—, —OCH$_2$CH$_2$N(R$^2$)—, —O—, —S—, —CH$_2$S—, —(CH$_2$)$_2$—NH—, or

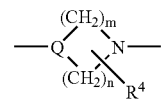

and

Z is $R^5$-phenyl, $R^5$-phenyl(C$_1$–C$_6$)alkyl, $R^5$-heteroaryl, diphenylmethyl, $R^6$—C(O)—, $R^6$—SO$_2$—, $R^6$—OC(O)—, $R^7$—N(R$^8$)—C(O)—, $R^7$—N(R$^8$)—C(S)—,

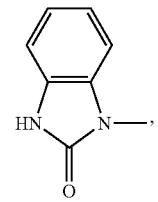

phenyl-CH(OH)—, or phenyl-C(=NOR$^2$)—; or when Q is

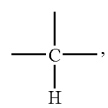

Z is also phenylamino or pyridylamino; or

Z and Y together are

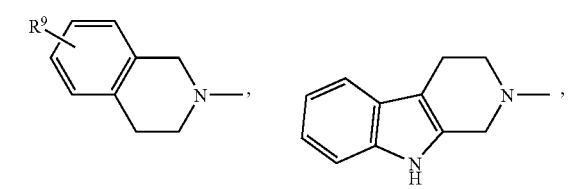

-continued

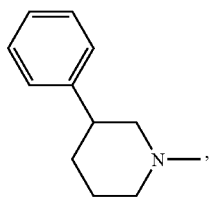
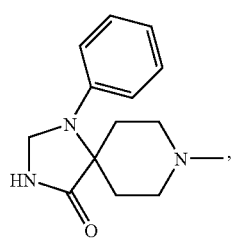

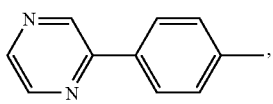
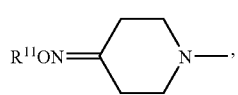

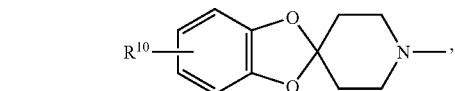

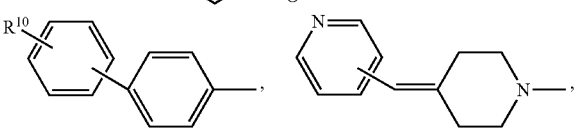

or an N-oxide thereof,

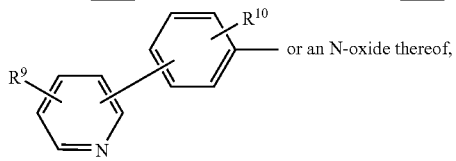

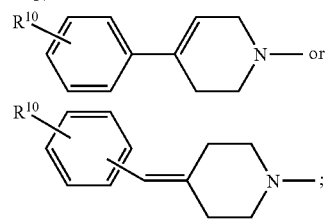

$R^1$ is 1 to 3 substituents independently selected from hydrogen, $C_1$–$C_6$-alkyl, —$CF_3$, halogen, —$NO_2$, —$NR^{12}R^{13}$, $C_1$–$C_6$ alkoxy, $C_1$–$C_6$ alkylthio, $C_1$–$C_6$ alkysulfinyl, and $C_1$–$C_6$ alkylsulfonyl;

$R^2$ and $R^3$ are independently selected from the group consisting of hydrogen and $C_1$–$C_6$ alkyl;

m and n are independently 2–3;

Q is

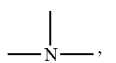 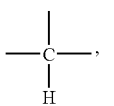 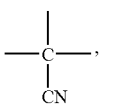 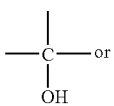 or

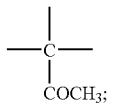

$R^4$ is 1–2 substituents independently selected from the group consisting of hydrogen and $C_1$–$C_6$alkyl, or two $R^4$ substituents on the same carbon can form =O;

$R^5$ is 1 to 5 substituents independently selected from the group consisting of hydrogen, halogen, $C_1$–$C_6$ alkyl, hydroxy, $C_1$–$C_6$ alkoxy, —CN, di-(($C_1$–$C_6$)alkyl)amino, —$CF_3$, —$OCF_3$, acetyl, —$NO_2$, hydroxy($C_1$–$C_6$)alkoxy, ($C_1$–$C_6$)-alkoxy($C_1$–$C_6$)alkoxy, di-(($C_1$–$C_6$)-alkoxy)($C_1$–$C_6$)alkoxy, ($C_1$–$C_6$)-alkoxy($C_1$–$C_6$)alkoxy-($C_1$–$C_6$)-alkoxy, carboxy($C_1$–$C_6$)-alkoxy, ($C_1$–$C_6$)-alkoxycarbonyl($C_1$–$C_6$)alkoxy, ($C_3$–$C_6$)cycloalkyl($C_1$–$C_6$)alkoxy, di-(($C_1$–$C_6$)alkyl)amino($C_1$–$C_6$)alkoxy, morpholinyl, ($C_1$–$C_6$) alkyl-$SO_2$—, ($C_1$–$C_6$)alkyl-SO—($C_1$–$C_6$)alkoxy, tetrahydropyranyloxy, ($C_1$–$C_6$)alkylcarbonyl($C_1$–$C_6$)-alkoxy, ($C_1$–$C_6$)-alkoxy, ($C_1$–$C_6$)-alkoxycarbonyl, ($C_1$–$C_6$) alkylcarbonyloxy($C_1$–$C_6$)-alkoxy, —$SO_2NH_2$, phenoxy,

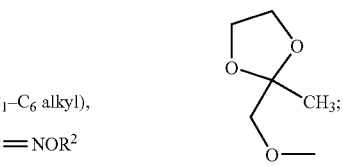

or adjacent $R^5$ substituents together are —O—$CH_2$—O—, —O—$CH_2CH_2$—O—, —O—$CF_2$—O— or —O—$CF_2CF_2$—O— and form a ring with the carbon atoms to which they are attached;

$R^6$ is ($C_1$–$C_6$)alkyl, $R^5$-phenyl, $R^5$-phenyl($C_1$–$C_6$)alkyl, thienyl, pyridyl, ($C_3$–$C_6$)-cycloalkyl, ($C_1$–$C_6$)alkyl-OC(O)—NH—($C_1$–$C_6$)alkyl—, di-(($C_1$–$C_6$)alkyl)aminomethyl, or

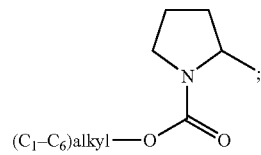

$R^7$ is ($C_1$–$C_6$)alkyl, $R^5$-phenyl or $R^5$-phenyl($C_1$–$C_6$)alkyl;

$R^8$ is hydrogen or $C_1$–$C_6$ alkyl; or $R^7$ and $R^8$ together are —($CH_2$)$_p$-A-($CH_2$)$_q$, wherein p and q are independently 2 or 3 and A is a bond, —$CH_2$—, —S— or —O—, and form a ring with the nitrogen to which they are attached;

$R^9$ is 1–2 groups independently selected from hydrogen, $C_1$–$C_6$ alkyl, hydroxy, $C_1$–$C_6$ alkoxy, halogen, —$CF_3$ and ($C_1$–$C_6$)alkoxy($C_1$–$C_6$)alkoxy;

$R^{10}$ is 1 to 5 substituents independently selected from the group consisting of hydrogen, halogen, $C_1$–$C_6$ alkyl, hydroxy, $C_1$–$C_6$ alkoxy, —CN, —$NH_2$, $C_1$–$C_6$alkylamino, di-(($C_1$–$C_6$)alkyl)amino, —$CF_3$, —$OCF_3$ and —S(O)$_{0-2}$ ($C_1$–$C_6$)alkyl;

$R^{11}$ is H, $C_1$–$C_6$ alkyl, phenyl, benzyl, $C_2$–$C_6$ alkenyl, $C_1$–$C_6$ alkoxy($C_1$–$C_6$)alkyl, di-(($C_1$–$C_6$)alkyl)amino($C_1$–$C_6$) alkyl, pyrrolidinyl($C_1$–$C_6$)alkyl or piperidino($C_1$–$C_6$)alkyl;

$R^{12}$ is H or $C_1$–$C_6$ alkyl; and $R^{13}$ is ($C_1$–$C_6$)alkyl-C(O)— or ($C_1$–$C_6$)alkyl-$SO_2$—.

Preferred compounds of formula I are those wherein R is $R^1$-furanyl, $R^1$-thienyl, $R^1$-pyrrolyl or $R^{10}$-phenyl, more preferably R¹-furanyl. R¹ is preferably hydrogen or halogen. Another group of preferred compounds is that wherein X is alkylene, preferably ethylene. Y is preferably

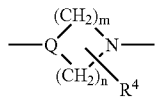

wherein Q is

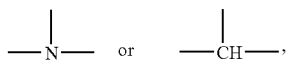

with Q preferably being nitrogen. Preferably, m and n are each 2, and $R^4$ is H. A preferred definition for Z is $R^5$-phenyl, $R^5$-heteroaryl, $R^6$—C(O)— or $R^6$—$SO_2$—. $R^5$ is preferably H, halogen, alkyl, alkoxy, hydroxyalkoxy or alkoxyalkoxy. $R^6$ is preferably $R^5$-phenyl.

Another aspect of the invention is a pharmaceutical composition comprising a therapeutically effective amount of a compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, and stroke, comprising administering a compound of formula I to a mammal in need of such treatment. In particular, the invention is drawn to the method of treating Parkinson's disease comprising administering a compound of formula I to a mammal in need of such treatment.

Another aspect of the invention is a process for preparing 5-amino-2-(R-substituted)-pyrazolo[4,3-e]-1,2,4-triazolo-[1,5-c]pyrimidines of formula II, which are intermediates useful in the preparation of compounds of formula I. The process of preparing compounds of formula II

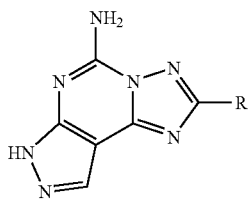

wherein R is as defined above, comprises (1) treating 2-amino-4,6-dihydroxypyrimidine

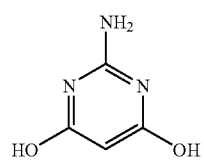

with $POCl_3$ in dimethylformamide (DMF) to obtain 2-amino4,6-dichloropyrimidine-5-carboxaldehyde

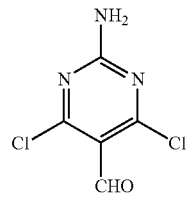

(2) treating carboxaldehyde VII with a hydrazide of the formula $H_2N$—NH—C(O)—R, wherein R is as defined above, to obtain

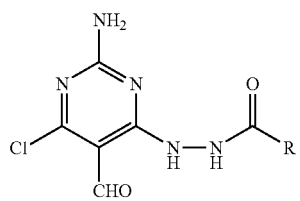

(3) treating the intermediate of formula VIII with hydrazine hydrate to form a pyrazolo ring, thus obtaining the intermediate of formula IX

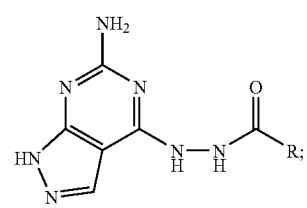

(4) forming the desired compound of formula II by dehydrative rearrangement.

A preferred aspect of the process is the dehydrative rearrangement of the intermediate of formula IX to obtain the 5-amino-2-(R-substituted)-pyrazolo[4,3-e]-1,2,4-triazolo[1,5-c]pyrimidine of formula II. Preferred embodiments of the process use 2-furoic hydrazide or 2-thienoylhydrazide in step 2, thus preparing compounds of formula II wherein R is 2-furyl or 2-thienyl.

Another aspect of the invention is a process for preparing 7-bromoalkyl-5-amino-2-(R-substituted )-pyrazolo[4,3-e]-1,2,4-triazolo-[1,5-c]pyrimidines of formula IIIa, which are intermediates useful in the preparation of compounds of formula I. The process of preparing compounds of formula IIIa

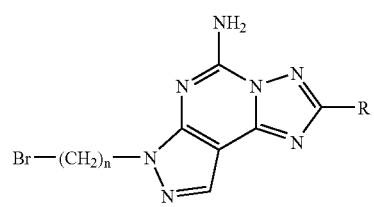

wherein R is as defined above, comprises (1) treating a chloride of formula VIII

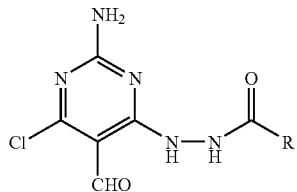

VIII with a hydroxyalkyl hydrazine of the formula HO—(CH$_2$)$_r$—NHNH$_2$, wherein r is 2–6, to obtain

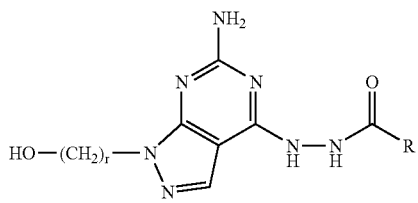

X (2) cyclizing the intermediate of formula X by dehydrative rearrangement to obtain the tricyclic intermediate of formula XI

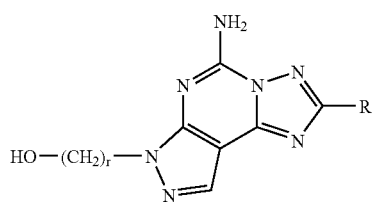

XI (3) converting the hydroxy compound of formula XI to the bromide of formula IIIa.

Still another aspect of the invention is a method of treating Parkinson's disease with a combination of a compound of formula I and one or more agents known to be useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising a compound of formula I and one or more agents known to be useful in the treatment of Parkinson's in a pharmaceutically acceptable carrier.

DETAILED DESCRIPTION

As used herein, the term alkyl includes straight or branched chains. Alkylene, referring to a divalent alkyl group, similarly refers to straight or branched chains. Cycloalkylene refers to a divalent cycloalkyl group. Cycloalkenyl refers to a C$_4$–C$_6$ cycloalkyl ring comprising one double bond.

Heteroaryl means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. R$^5$-substituted heteroaryl refers to such groups wherein substitutable ring carbon atoms have a substituent as defined above.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula I can be prepared by known methods from starting materials either known in the art or prepared by methods known in the art; see, for example, WO 95/01356 and *J. Med. Chem.*, 39 (1996) 1164–1171.

Preferably, the compounds of formula I are prepared by the methods shown in the following reaction schemes. In Scheme 1, alkylation of a 5-amino-pyrazolo[4,3-e]-[1,2,4]-triazolo[1,5-c]pyrimidine of formula II is used to prepare compounds of formula I:

Scheme 1:

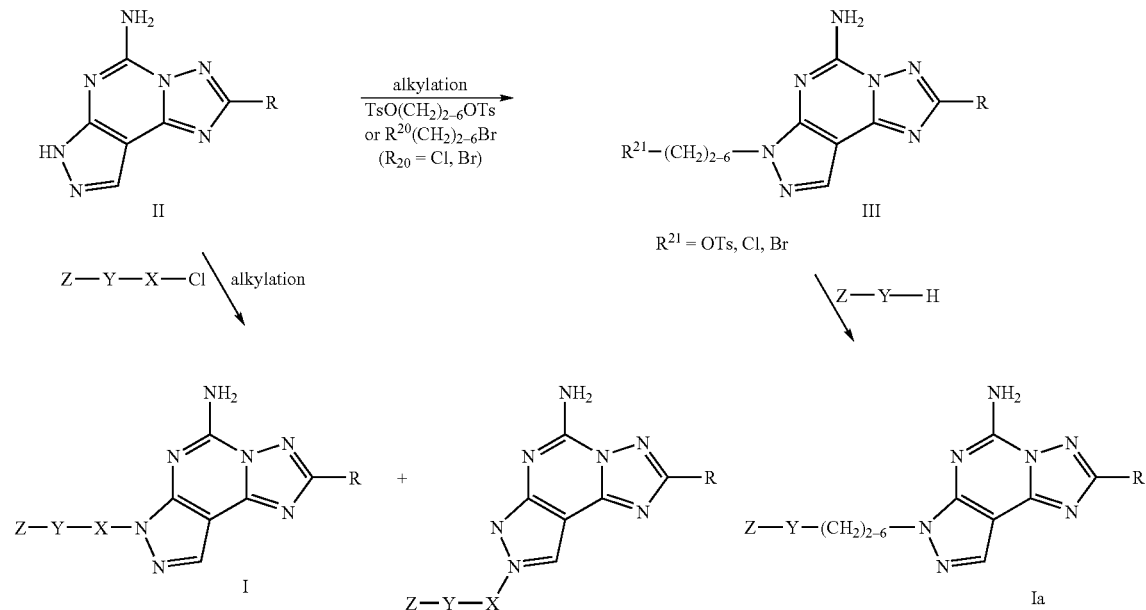

Starting materials of formula II can be reacted with an alkyl diol ditosylate and a base such as NaH in an inert solvent such as dimethylformamide (DMF), or with a chloro-bromo- or dibromo-alkyl compound under similar conditions, to obtain the alkyl-substituted intermediate of formula III. The compound of formula III is then reacted with an amine of the formula Z-Y—H in an inert solvent such as DMF at an elevated temperature to obtain a compound of formula Ia, i.e., a compound of formula I wherein X is alkylene.

Alternatively, staring materials of formula II can be reacted with a compound of formula Z-Y—X—Cl and a base such as NaH in an inert solvent such as DMF to obtain a mixture of a 7-substituted compound of formula I and the corresponding 8-substituted compound.

To prepare compounds of formula I wherein Y is piperazinyl and Z is $R^6$—C(O)—, $R^6$—$SO_2$—, $R^6$—OC(O)—, $R^7$—N($R^8$)—C(O)— or $R^7$—N($R^8$)—C(S)—, a compound of formula I wherein Z-Y is 4-t-butoxycarbonyl-1-piperazinyl is deprotected, for example by reaction with an acid such as HCl. The resultant free piperazinyl compound, IV, is treated according to procedures well known in the art to obtain the desired compounds. The following Scheme 2 summarizes such procedures:

Scheme 2:

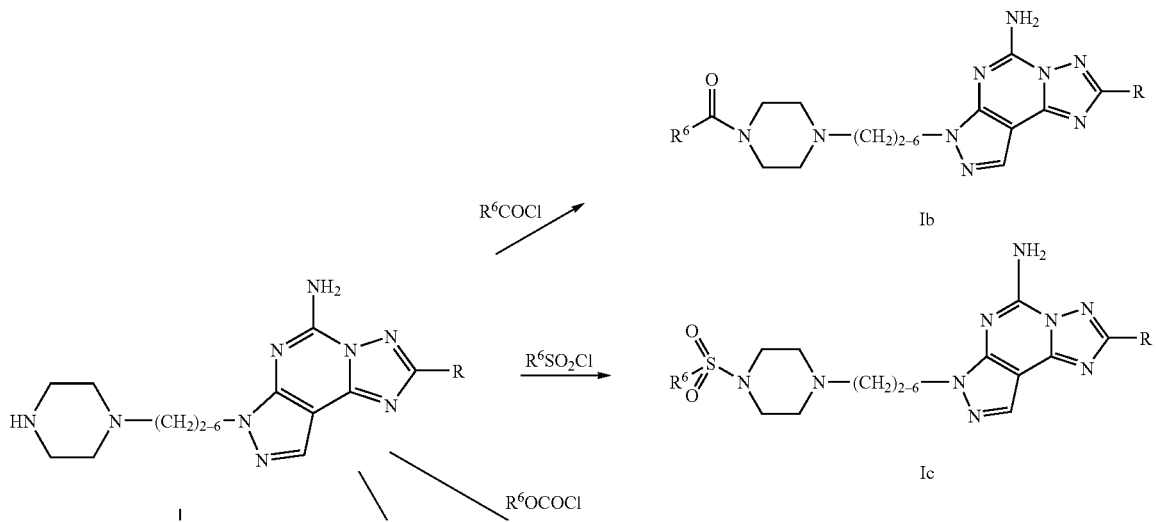

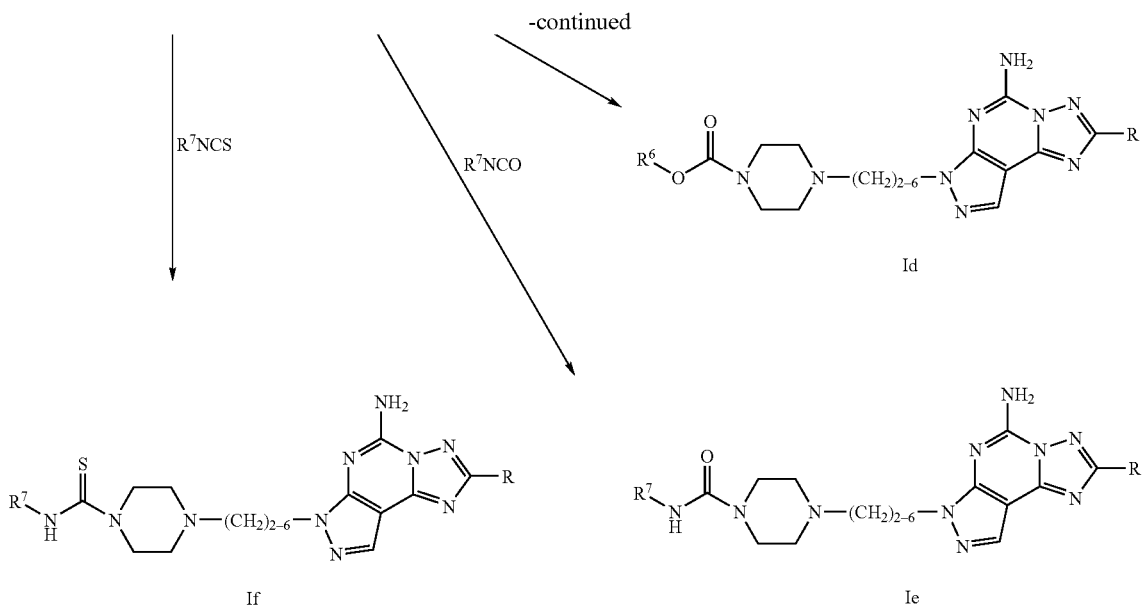

Another method for preparing compounds of formula I is shown in Scheme 3:

Scheme 3:

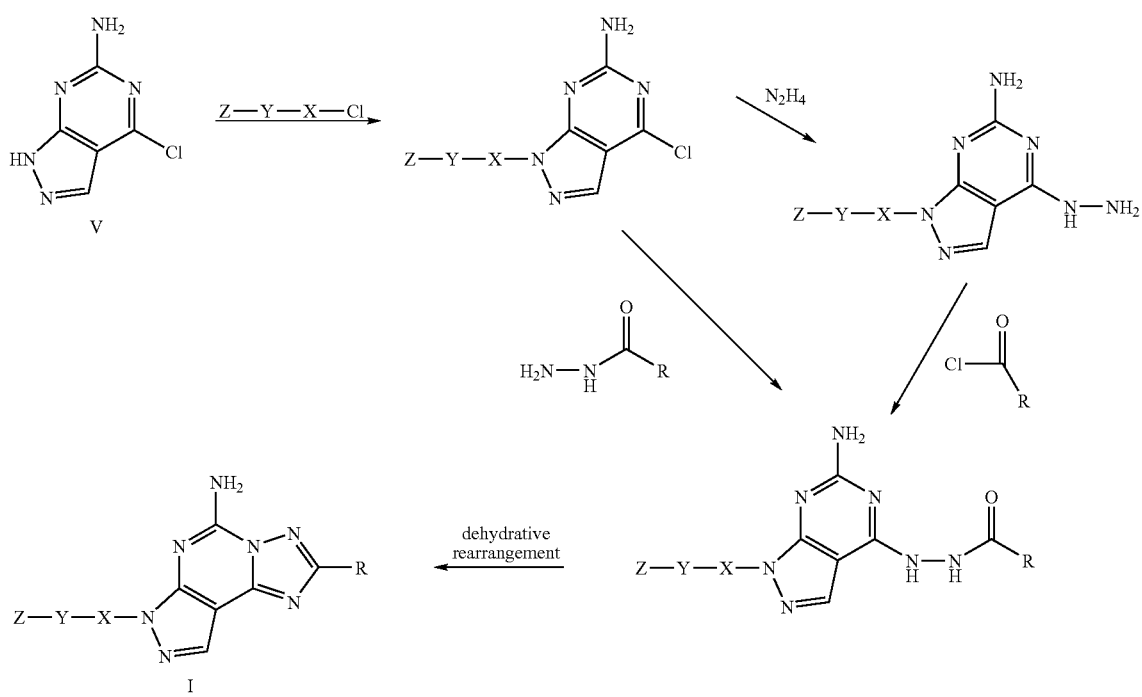

In this procedure, chloropyrazolo-pyrimidine V is reacted with a compound of formula Z—Y—X—Cl in a manner similar to the alkylation procedure of Scheme 1, and the resultant intermediate is reacted with a hydrazide of formula $H_2N$—NH—C(O)—R (or with hydrazine hydrate, followed by a compound of formula Cl—C(O)—R). The resultant hydrazide undergoes dehydrative rearrangement, e.g., by treatment with N,O-bis-(trimethylsilyl)acetamide (BSA) or a combination of BSA and hexamethyidisilazane (HMDS) and at elevated temperatures.

Starting materials are known or can be prepared by processes known in the art. However, compounds of formula II are preferably prepared by the novel process disclosed above and described in further detail here.

In the first step of the process, 2-amino-4,6-dihydroxypyrimidine (VI) is converted to the corresponding 4,6-dichloro-5-carboxaldehyde by treatment with $POCl_3$ or $SOCl_2$ in DMF as described in *Helv. Chim. Acta*, 69 (1986), 1602–1613. The reaction is carried out at an elevated temperature, preferably about 100° C., for 2 to 8 hours, preferably about 5 hours.

In the second step, 2-amino-4,6-dichloropyrimidine-5-carboxaldehyde (VII) is treated with a hydrazide of the formula $H_2N$—NH—C(O)—R, wherein R is as defined above, to obtain the compound of formula VIII; the compound of formula VI and the hydrazide are used in a molar ratio of approximately 1:1, with a slight excess of the hydrazide being preferred. The reaction is carried out at room temperature or up to about 80° C. in a solvent such as $CH_3CN$ or DMF. The reaction time is about 16 hours (e.g., overnight).

In the third step, the compound of formula VIII is heated at 60–100° C. with 1–5 equivalents of hydrazine hydrate in a solvent such as $CH_3CN$ or DMF for 1–24 hours to obtain the compound of formula IX.

In the last step, the compound of formula IX undergoes dehydrative rearrangement by treatment with a mixture of HMDS and BSA or with BSA alone. The reaction is carried out at elevated temperatures, preferably about 120° C., for about 16 hours (e.g., overnight)

After each step of the process, the crude material is purified by conventional methods, e.g., extraction and/or recrystallization.

Compared to previously published methods for preparing the intermediate of formula II, this method proceeds in fewer steps, under milder reaction conditions and with much higher yield.

The compounds of formulas V and VII are known (*Helv. Chim. Acta*, 69 (1986), 1602–1613).

Another method for preparing compounds of formula I is illustrated in the following Scheme 4.

Scheme 4:

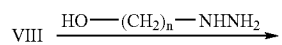

-continued

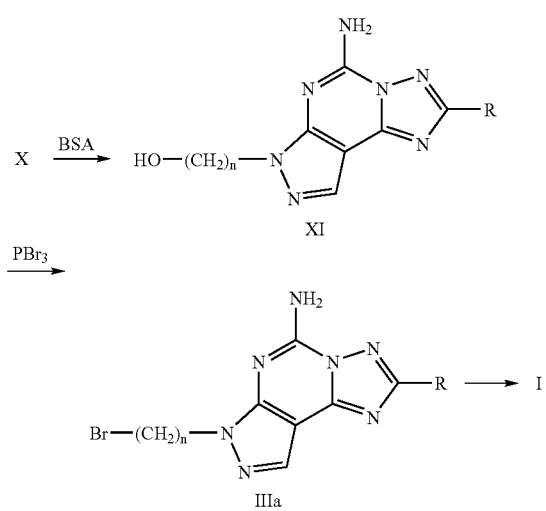

Chloride VIII is treated with a hydroxyalkyl-hydrazine in an inert solvent such as ethanol at temperatures from ambient to 100° C. to furnish derivative X. This is subjected to dehydrative cyclization, similarly to IX, such as with BSA, to provide tricyclic XI. Tricyclic XI is then converted to bromide IIIa with $PBr_3$ at elevated temperature from 80° C. to 150° C. for 1 to 24 hours. Intermediate XI can also be converted into the tosylate analogous to IIIa by toluenesulfonyl chloride and base. Bromide IIIa is converted to compounds of formula I as described above for III.

Another method for preparing compounds of formula I is illustrated in the following Scheme 5:

Scheme 5:

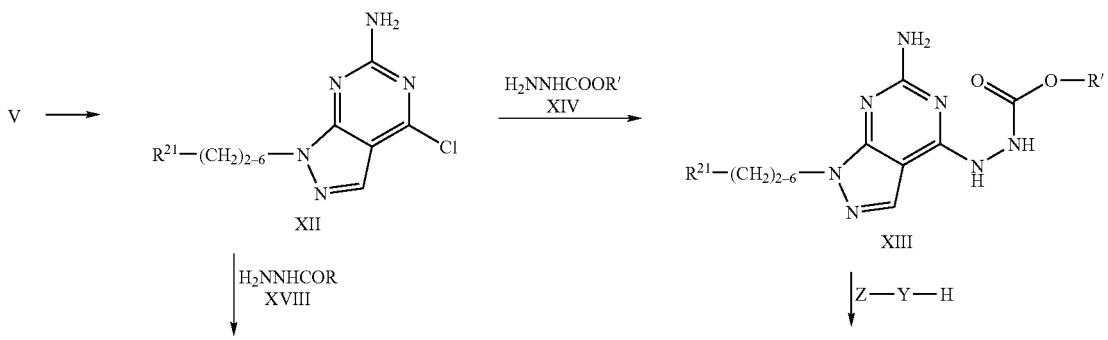

-continued

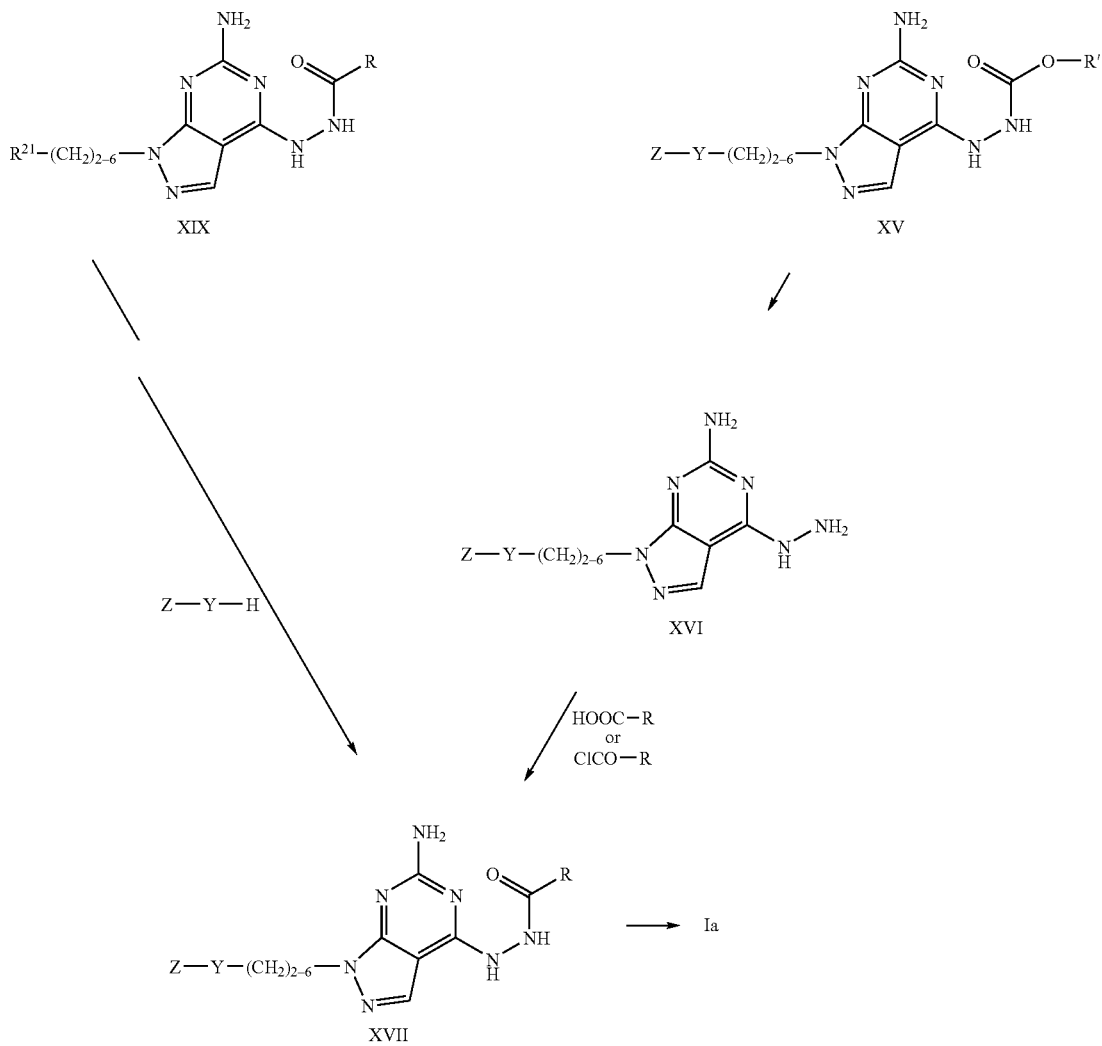

In analogy to Scheme 1, chloride V is converted into alkylated compound XII, and this is further reacted with carbazate XIV, where R' is preferably t-butyl or benzyl, to obtain derivative XIII. A solvent such as DMF may be employed at a temperature of 60–120° C. This is then reacted as in Scheme 1 to furnish XV. The R' group is next removed, such as removal of a t-butyl group with HCl or TFA, furnishing hydrazine XVI. Acylation of XVI furnishes XVII, which is subjected to dehydrative cyclization as described above to provide desired Ia. Alternatively, XII may be reacted with a hydrazide XVIII to obtain XIX, which can be converted to XVII analogously to preparation of XV.

Using the above procedures, the following compounds were prepared.

Preparation 1

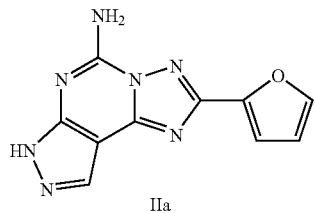

-continued

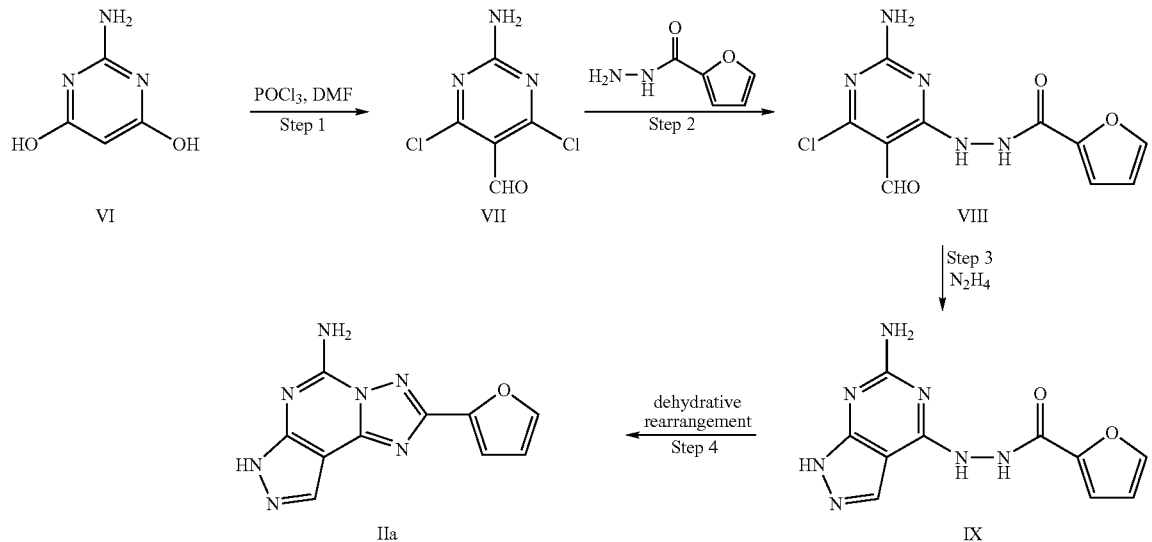

Step 1: Stir POCl$_3$ (84 ml, 0.9 mol) and chill to 5-10° C. while adding DMF (17.8 ml, 0.23 mol) drop-wise. Allow the mixture to warm to room temperature (RT) and add 2-amino-4,6-dihydroxypyrimidine VI (14 g, 0.11 mol) portion-wise. Heat at 100° C. for 5 h. Strip off excess POCl$_3$ under vacuum, pour the residue into ice water, and stir overnight. Collect solids by filtration and recrystallize the dried material from a filtered ethyl acetate (EtOAc) solution to give the aldehyde, VII, m.p. 230° (dec). Mass spectrum: M+=192. PMR (DMSO): δ 8.6(δ, 2H); δ 10.1 (s, 1H).

Step 2: Stir a mixture of the product of Step 1 (0.38 g, 2 mmol) and 2-furoic hydrazide (0.31 g, 2.5 mmol) in CH$_3$CN (50 ml) containing N,N-diisopropylethylamine (0.44 ml, 2.5 mmol) overnight at RT. Solvent strip the reaction mixture, and partition the residue between EtOAc and water. Dry the organic layer over MgSO$_4$, remove the solvent, and recrystallize the residue from CH$_3$CN to give the desired compound VIII. Mass spectrum: MH+=282.

Step 3: Add hydrazine hydrate (75 mg, 1.5 mmol) to a hot CH$_3$CN solution of the product of Step 2 (0.14 g, 0.5 mmol). Reflux 1 h. Cool to RT and collect the yellow product IX. Mass spectrum: MH+=260.

Step 4: Heat the product of Step 3 (5.4 g, 0.021 mol) in a mixture of hexamethyl-disilazine (100 ml) and N,O-bis (trimethylsilyl) acetamide (35 ml) at 120° C. overnight. Remove volatiles under vacuum and slurry the residue in hot water to give a solid precipitate. Recrystallize from 80% aqueous acetic acid to give the title compound. M.P.>300° C. Mass spectrum: MH+=242.

Preparation 2

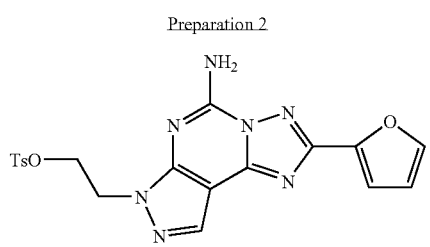

-continued

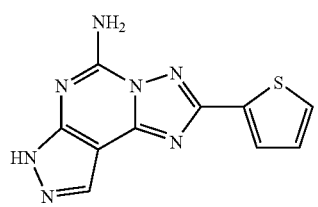

Combine the product of Preparation 1 (6.0 g, 25 mmol), ethylene glycol ditosylate (11.1 g, 30 mmol), and NaH (60% in oil, 1.19 g, 30 mmol) in dry DMF (30 ml). Stir under N$_2$ for 24 h and filter to obtain the title compound as a cream solid (PMR in DMSO: δ4.47+4.51 triplets, 8.03 s). Isolate additional material by chromatography of the filtrate.

Preparation 3

In a similar manner to Preparation 1, but employing 2-thienoylhydrazide, prepare the title compound as a yellow solid, mass spectrum: MH+=258.

Preparation 4

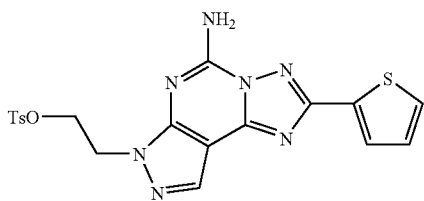

In a similar manner to Preparation 2, but using the product of Preparation 3, prepare the title compound as a yellow solid, PMR (DMSO) δ 4.49+4.54 triplets, 8.05 s.

Preparation 5

Arylpiperazines 1-(2,4-Difluorophenyl)piperazine is prepared from 2,4-difluorobromobenzene. To the bromide (8.0 g, 41.4 mmol), piperazine (21.4 g, 249 mmol), sodium t-butoxide (5.6 g, 58 mmol) and BINAP (1.55 g, 2.5 mmol) in toluene (20 ml), add $Pd_2(dba)_3$ (0.477 g, 0.83 mmol). Heat the mixture at 110° C. under $N_2$ for 20 h. Allow to cool and extract with 1N HCl. Basify the extract with NaOH to pH=10, extract with $CH_2Cl_2$, dry and concentrate to obtain the title compound as a brown oil.

In a similar fashion, prepare the following arylpiperazines (Me is methyl):

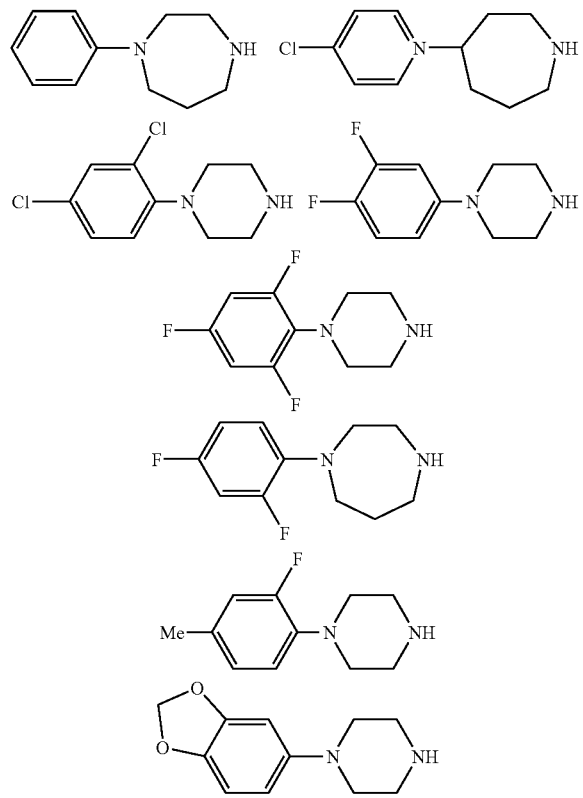

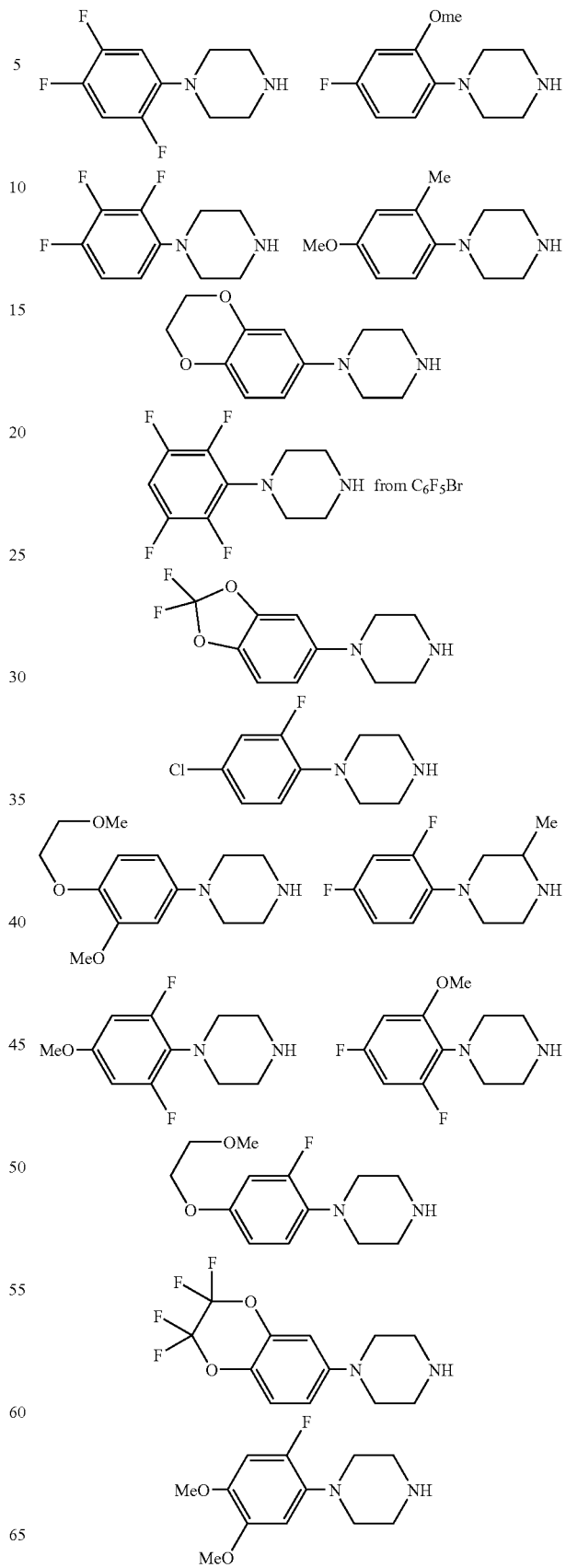

-continued

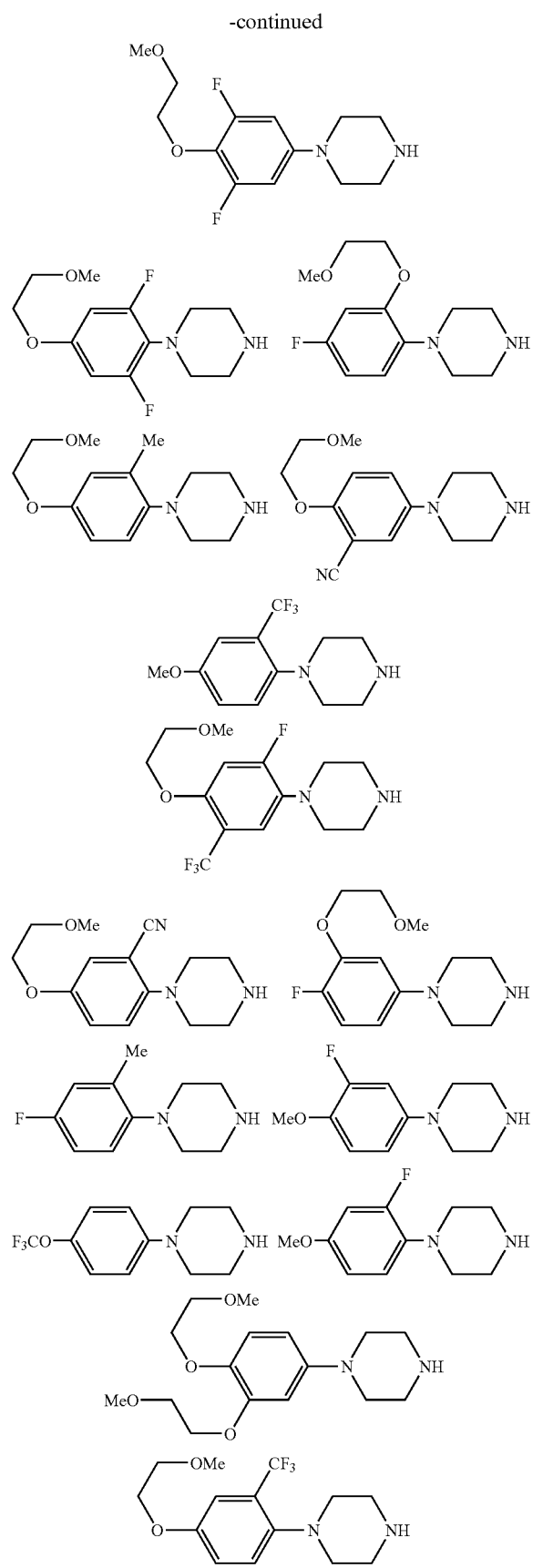
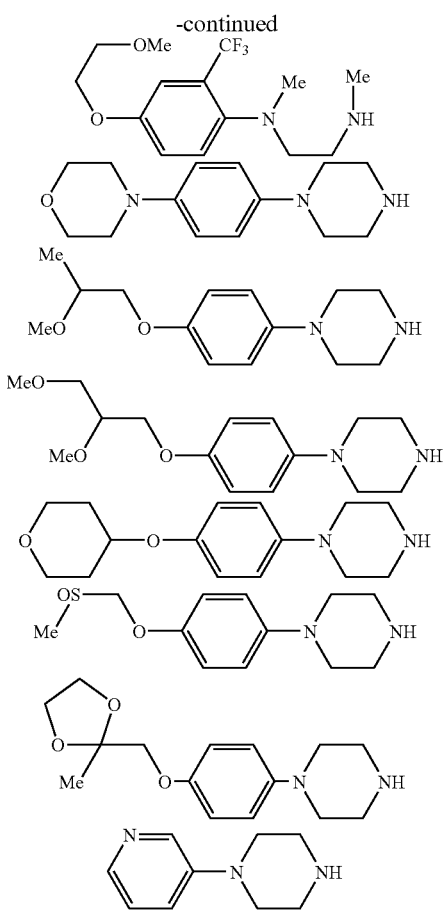

1-(5-Ethyl-2-pyrimidinyl)piperazine is prepared from 2-chloro-5-ethylpyrimidine. Heat the chloride (2.0 g, 14 mmol) and piperazine (3.0 g, 35 mmol) in EtOH (70 ml) at 90° C. for 2 h in a sealed vessel. Concentrate and partition between $CH_2Cl_2$ and 2N NaOH. Dry the organic with $MgSO_4$ and concentrate. Chromatograph the crude product on silica ($CH_2Cl_2$—$CH_3OH$) to obtain the piperazine as a yellow oil.

In a similar fashion, prepare the following piperazines from the appropriate chloride:

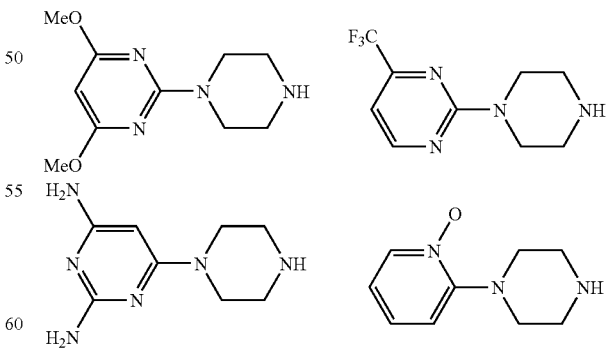

1-(4-Cyano-2-fluorophenyl)piperazine is prepared from 3,4-difluorobenzonitrile. Heat the nitrile (2.0 g, 14.4 mmol), piperazine (6.2 g, 72 mmol) and $K_2CO_3$ (2.4 g, 17 mmol) in toluene (10 ml) at reflux for 22 h. Allow to cool, and extract with 1N HCl. Basify with NaOH to pH=10. Extract with CH$_2$Cl$_2$ and wash with water and then brine. Dry the organic with MgSO$_4$ and concentrate to give the piperazine as a white solid.

In a similar fashion, prepare the following piperazines from the appropriate fluoride (Et is ethyl):

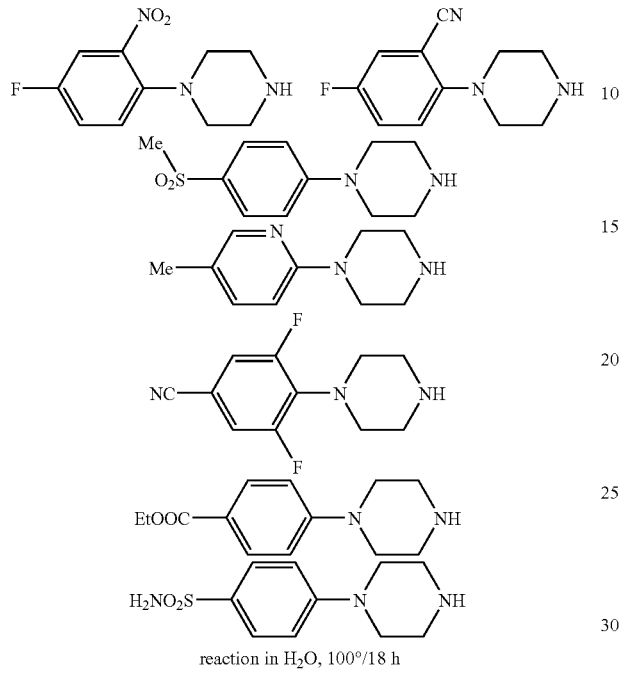

1-(4-(2-Methoxyethoxy)phenyl)piperazine is prepared from 4-(4-hydroxy-phenyl)-1-acetylpiperazine. To NaH (60% in mineral oil, 0.79 g, 20 mmol) in DMF (25 ml) add the phenol (3.0 g, 13.6 mmol), followed by 2-bromoethyl methyl ether (2.27 g, 16.3 mmol). Stir at RT 18 h, concentrate, and partition between EtOAc and 5% citric acid. Wash the organic with 1N NaOH, then brine. Dry over MgSO$_4$, and concentrate to obtain the alkylated product as a white solid. Heat this material (2.2 g, 7.9 mmol) in 6N HCl (30 ml) at reflux for 1 h. Allow to cool and basify to pH=10 with NaOH. Extract with CH$_2$Cl$_2$ and wash with water and then brine. Dry the organic with MgSO$_4$ and concentrate to give the piperazine as a yellow oil.

In a similar fashion (except basic hydrolysis is employed for the cyclopropyl-methyl ether) prepare the following piperazines:

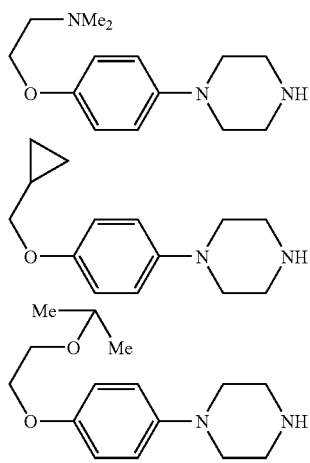

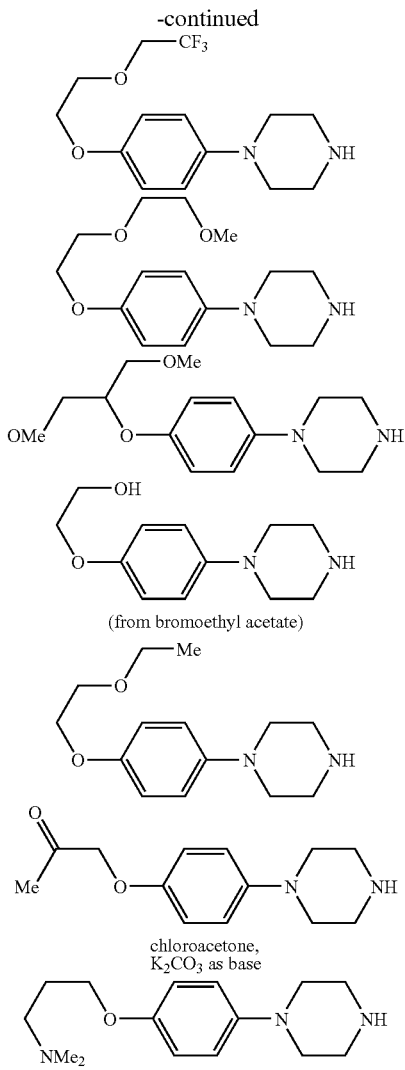

4-(2-Methylaminoethoxy)fluorobenzene is prepared from 4-(2-bromo-ethoxy)-fluorobenzene. Combine the bromide (1.0 g, 4.6 mmol) in CH$_3$OH (5 ml) with CH$_3$NH$_2$ in CH$_3$OH (2M, 46 ml, 92 mmol) in a sealed vessel. Heat at 60° C. for 18 h, concentrate, and partition between EtOAc and sat. NaHCO$_3$. Wash the organic with brine, dry with MgSO$_4$, and concentrate to obtain the amine as a yellow oil.

N-methyl-2-(4-(2-methoxyethoxy)phenoxy)ethylamine was prepared in two steps. Combine 4-(2-methoxyethoxy) phenol (1.68 g, 10.0 mmol), 1,2-dibromoethane (16.9 g, 90 mmol), and K$_2$CO$_3$ (2.76 g, 20 mmol) in CH$_3$CN (20 ml) and DMF (10 ml). Heat at reflux 22 h, allow to cool, filter, and partition between ether (Et$_2$O) and 1N NaOH. Wash with brine, dry over MgSO$_4$, and concentrate to provide the bromoethyl ether as beige solid. Combine this (0.97 g, 3.5 mmol) with 2M CH$_3$NH$_2$/CH$_3$OH (35 ml). Heat in a sealed tube (65° C., 18 h), concentrate, and partition between Et$_2$O and 1N NaHCO$_3$. Wash with brine, dry MgSO$_4$, and concentrate to provide the amine as an orange oil.

1-Phenyl-2-piperazinone is prepared from 4-benzyloxycarbonyl-1-phenyl-2-piperazinone. Combine this material (1.61 g, 5.2 mmol) with 10% Pd/C (0.4 g) in EtOH (50 ml) and 1N HCl (6 ml). Hydrogenate at 45 psi for 2 h and filter. Concentrate and chromatograph the residue on silica (eluting with CH$_2$Cl$_2$:CH$_3$OH:NH$_4$OH) to obtain the piperazinone as a cream solid.

Preparation 6

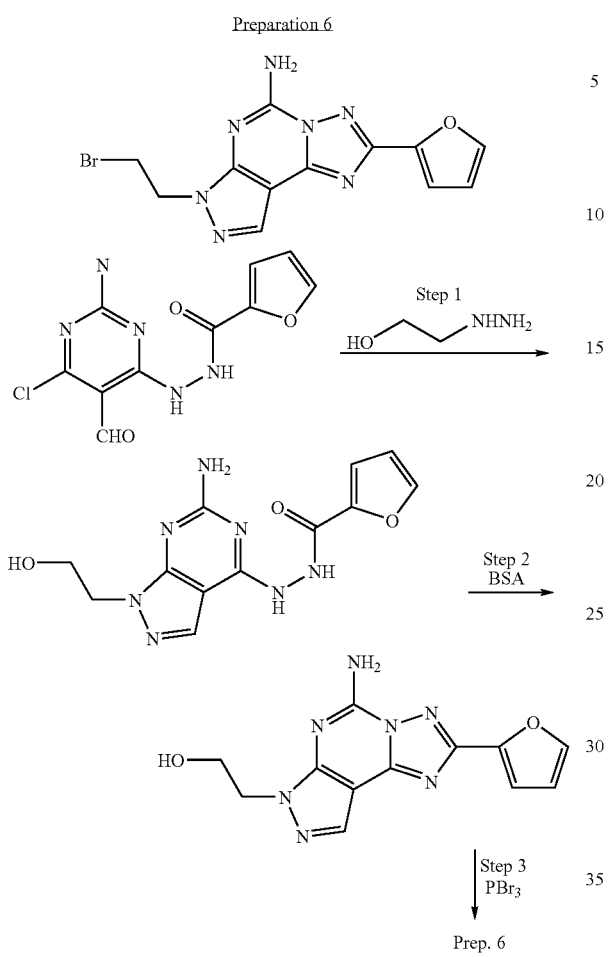

Step 1: Dissolve the product of Preparation 1, Step 2 (0.56 g, 2.0 mmol) in hot CH$_3$CN (200 ml). Add 2-hydroxyethylhydrazine (0.51 g, 6.0 mmol). Heat at reflux 2 h and concentrate. Treat with 25 ml water and stir to give a solid. Collect and dry to give the alcohol, MS: m/e=304 (M+1).

Step 2: Heat the product of Step 1 (0.10 g, 0.33 mmol) in BSA (10 ml) for 4 h at 115° C. Concentrate in vacuo and warm with aqueous CH$_3$OH. Collect and dry to give the cyclization product, MS: m/e=286 (M+1).

Step 3: Combine the product of Step 2 (0.285 g, 1.0 mmol) and PBr$_3$ (2.0 ml, 21 mmol). Heat at 145° C. for 2 h, cool, and pour onto ice. Filter and dry the solid. Recrystallize from CH$_3$OH to obtain the title compound, MS: m/e=348+350 (M+1).

Preparation 7

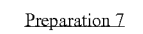
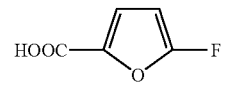

Combine 5-bromo-2-furoic acid (0.50 g, 2.6 mmol) and NaHCO$_3$ (0.44 g, 5.2 mmol) in hexane (6 ml) and water (5.2 ml). Add Selectfluor® (0.98 g, 2.8 mmol) and stir 2 h. Separate the hexane layer and dry over MgSO$_4$ to provide a solution of 2-bromo-5-fluorofuran. Dilute with THF (6 ml) and cool to −78° C. Add 2.5M n-BuLi/hexane (4.2 ml, 11 mmol). Stir 10 min., add excess dry ice, and stir 1 h additional. Treat with 1N HCl, extract with CH$_2$Cl$_2$, and dry over MgSO$_4$. Concentrate and dry to obtain the title compound as a white solid, PMR (CDCl$_3$) δ6.70+7.28.

EXAMPLE 1

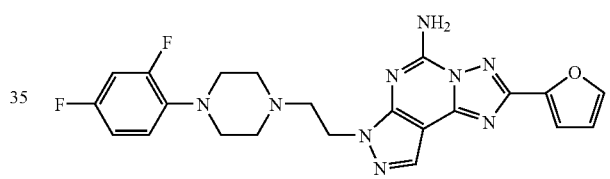

Combine the tosylate of Preparation 2 (0.55 g, 1.25 mmol) and 1-(2,4-difluorophenyl)piperazine (0.50 g, 2.5 mmol) in DMF (7 ml) and heat at 80° C. for 20 h. Concentrate and purify by flash column chromatography (CH$_2$Cl$_2$, CH$_3$OH+ NH$_3$) to obtain the title compound as a cream solid, mass spectrum m/e=466 (M+H).

In similar fashion, prepare the following compounds:

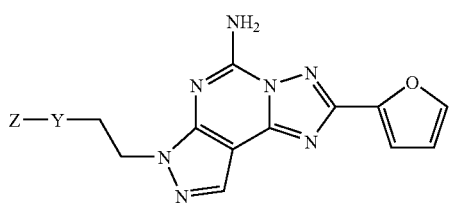

| Example | Z—Y— | MS, [M+1] m/e |
|---|---|---|
| 1-2 |  | 430 |

-continued

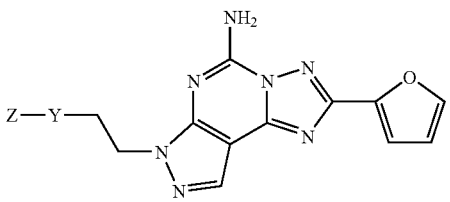

| Example | Z—Y— | MS, [M+1] m/e |
|---|---|---|
| 1-3 | 3,4-dichlorophenyl-4-methylpiperazinyl | 498, 500, 502 |
| 1-4 | 3-(trifluoromethyl)phenyl-4-methylpiperazinyl | 498 |
| 1-5 | benzyl-4-methylpiperazinyl | 444 |
| 1-6 | 2-pyridyl-4-methylpiperazinyl | 431 |
| 1-7 | 2-methoxyphenyl-4-methylpiperazinyl | 460 |
| 1-8 | 4-fluorophenyl-4-methylpiperazinyl | 448 |
| 1-9 | phenyl-NH-CH2CH2-NH- | 404 |
| 1-10 | diphenylmethyl-4-methylpiperazinyl | 520 |
| 1-11 | 4-(trifluoromethyl)phenyl-4-methylpiperazinyl | 498 |
| 1-12 | 4-chloro-3-(trifluoromethyl)phenyl-4-methylpiperazinyl | 532, 534 |

-continued

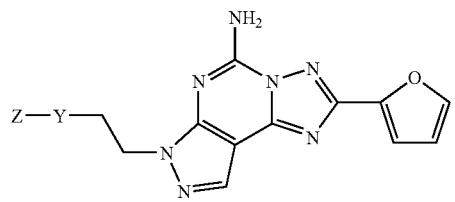

| Example | Z—Y— | MS, [M+1] m/e |
|---|---|---|
| 1-13 | 4-chloro-phenyl-(2-methyl)-4-methylpiperazinyl | 478, 480 |
| 1-14 | 2-methoxy-5-chloro-phenyl-(4-methylpiperazinyl) | 494, 496 |
| 1-15 | phenyl-(4-methyl-1,4-diazepanyl) | 444 |
| 1-16 | 4-chloro-phenyl-(4-methyl-1,4-diazepanyl) | 478, 480 |
| 1-17 | 4-chloro-phenyl-(4-methylpiperazinyl) | 464, 466 |
| 1-18 | pyrimidin-2-yl-(4-methylpiperazinyl) | 432 |
| 1-19 | Boc-(3-methyl-4-methylpiperazinyl) | 468 |
| 1-20 | pyridin-4-yl-(4-methylpiperazinyl) | 431 |
| 1-21 | 4-acetyl-phenyl-(4-methylpiperazinyl) | 472 |
| 1-22 | 4-bromo-phenyl-(4-methylpiperazinyl) | 508, 510 |
| 1-23 | 3,4-dimethoxy-phenyl-(4-methylpiperazinyl) | 490 |

-continued
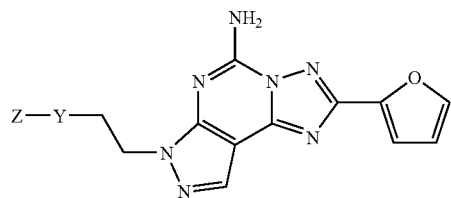
| Example | Z—Y— | MS, [M+1] m/e |
|---|---|---|
| 1-24 | 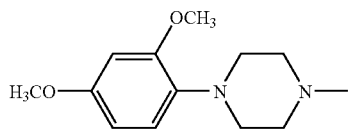 | 490 |
| 1-25 | 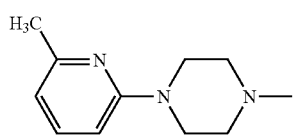 | 445 |
| 1-26 | 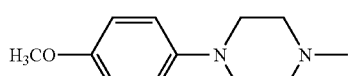 | 460 |
| 1-27 | 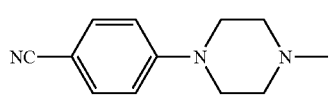 | 455 |
| 1-28 | 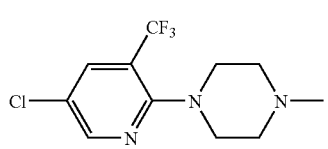 | 533, 535 |
| 1-29 | 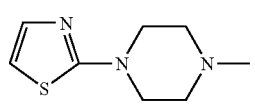 | 437 |
| 1-30 | 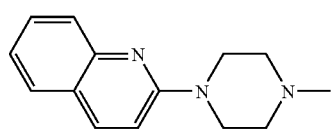 | 481 |
| 1-31 | 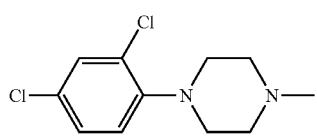 | 498, 500, 502 |
| 1-32 | 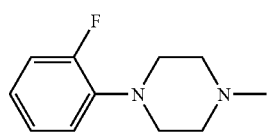 | 448 |
| 1-33 | 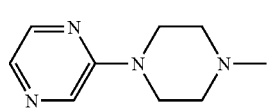 | 432 |
| 1-34 | 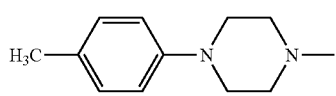 | 444 |

-continued
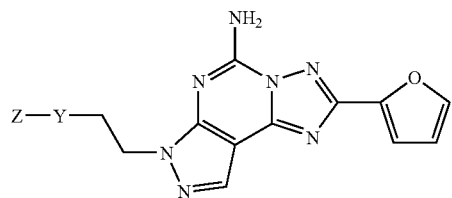
| Example | Z—Y— | MS, [M+1] m/e |
|---|---|---|
| 1-35 | 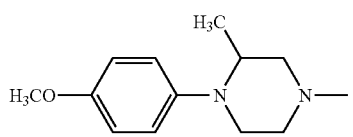 | 474 |
| 1-36 | 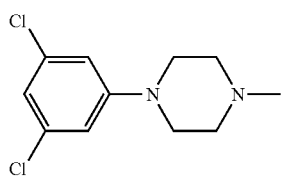 | 498, 500, 502 |
| 1-37 | 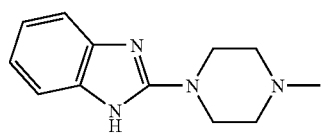 | 470 |
| 1-38 | 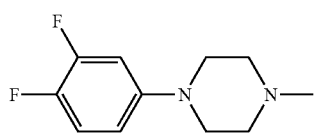 | 466 |
| 1-39 | 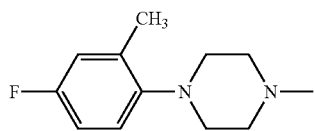 | 462 |
| 1-40 | 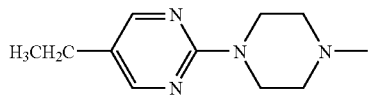 | 460 |
| 1-41 | 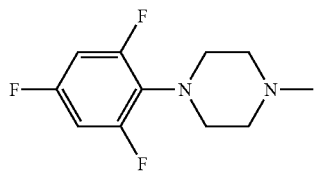 | 484 |
| 1-42 | 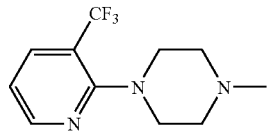 | 499 |
| 1-43 | 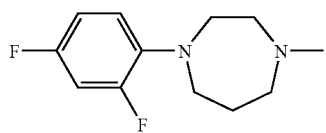 | 480 |

-continued
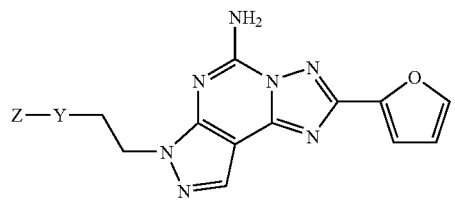
| Example | Z—Y— | MS, [M+1] m/e |
|---|---|---|
| 1-44 | 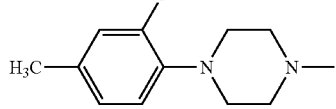 | 462 |
| 1-45 | 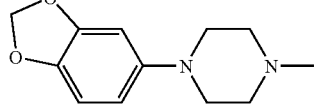 | 474 |
| 1-46 | 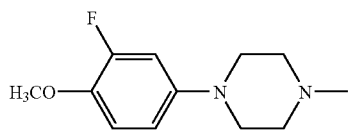 | 478 |
| 1-47 | 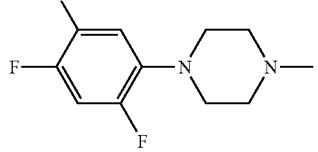 | 484 |
| 1-48 | 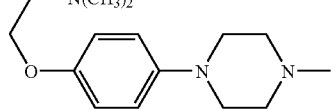 | 517 |
| 1-49 | 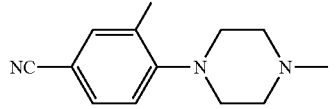 | 473 |
| 1-50 | 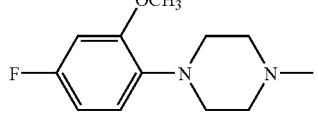 | 478 |
| 1-51 | 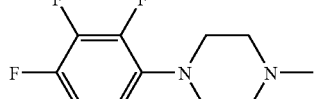 | 484 |
| 1-52 | 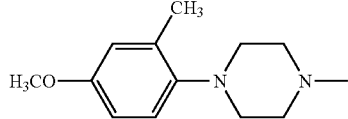 | 474 |

-continued
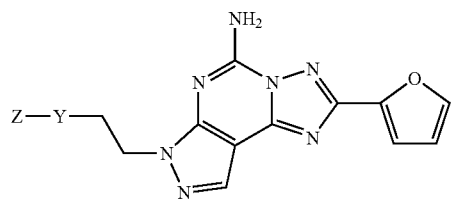
| Example | Z—Y— | MS, [M+1] m/e |
|---|---|---|
| 1-53 | 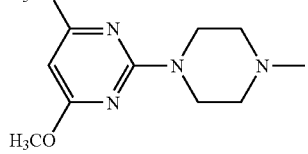 | 492 |
| 1-54 | 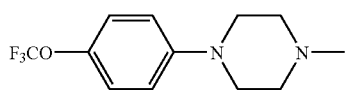 | 514 |
| 1-55 | 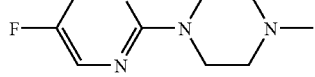 | 450 |
| 1-56 | 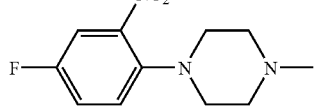 | 493 |
| 1-57 | 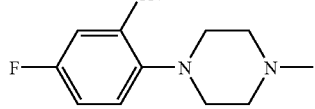 | 473 |
| 1-58 | 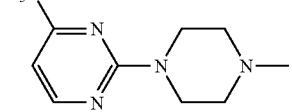 | 500 |
| 1-59 | 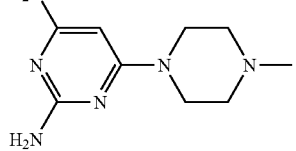 | 462 |
| 1-60 | 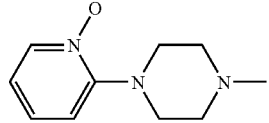 | 447 |
| 1-61 | 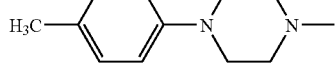 | 445 |

-continued

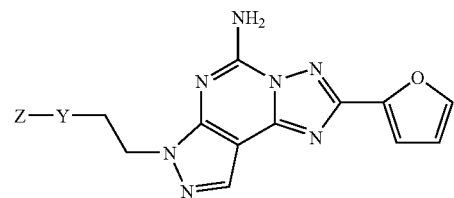

| Example | Z—Y— | MS, [M+1] m/e |
|---|---|---|
| 1-62 | 4-(4-methylpiperazin-1-yl)phenoxy-CH2CH2-OCH3 | 504 |
| 1-63 | 2,3-dihydro-benzo[1,4]dioxin-6-yl-(4-methylpiperazin-1-yl) | 488 |
| 1-64 | 2,3,5,6-tetrafluoro-4-(4-methylpiperazin-1-yl)phenyl | 502 |
| 1-65 | 2,2-difluoro-benzo[1,3]dioxol-5-yl-(4-methylpiperazin-1-yl) | 510 |
| 1-66 | 4-chloro-2-fluoro-phenyl-(4-methylpiperazin-1-yl) | 482, 484 |
| 1-67 | 2-fluoro-4-methoxy-phenyl-(4-methylpiperazin-1-yl) | 478 |
| 1-68 | 3-methoxy-4-(2-methoxyethoxy)phenyl-(4-methylpiperazin-1-yl) | 534 |
| 1-69 | 2,4-difluoro-phenyl-(3,4-dimethylpiperazin-1-yl) | 480 |
| 1-70 | 4-methoxy-2,6-difluoro-phenyl-(4-methylpiperazin-1-yl) | 496 |

-continued
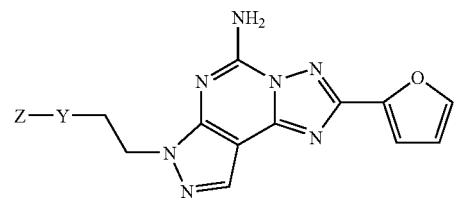
| Example | Z—Y— | MS, [M+1] m/e |
|---|---|---|
| 1-71 | 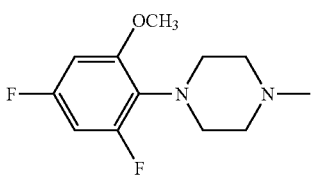 | 496 |
| 1-72 | 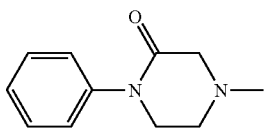 | 444 |
| 1-73 | 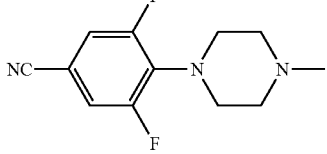 | 491 |
| 1-74 | 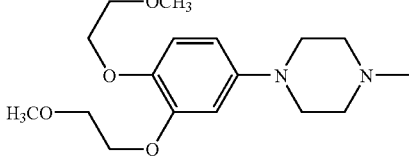 | 578 |
| 1-75 | 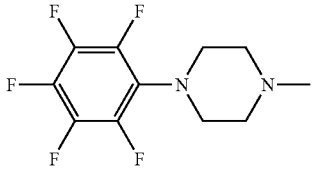 | 520 |
| 1-76 | 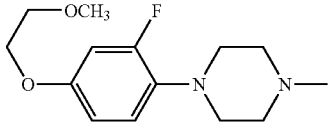 | 522 |
| 1-77 | 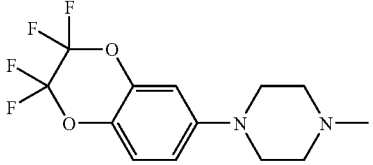 | 560 |
| 1-78 | 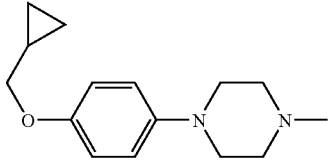 | 500 |

-continued
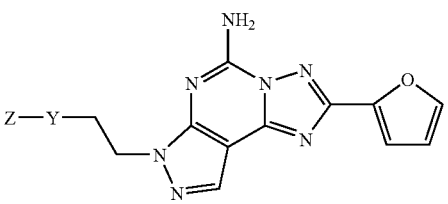
| Example | Z—Y— | MS, [M+1] m/e |
|---|---|---|
| 1-79 | 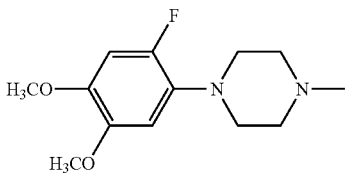 | 508 |
| 1-80 | 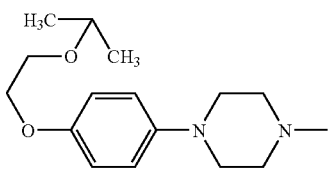 | 532 |
| 1-81 | 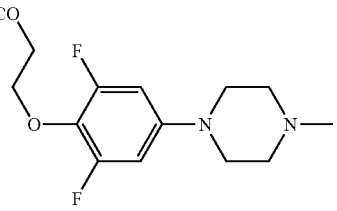 | 540 |
| 1-82 | 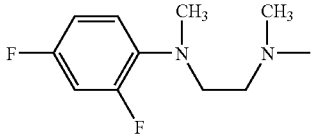 | 468 |
| 1-83 | 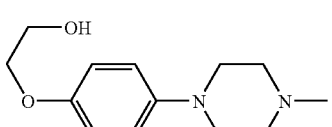 | 490 |
| 1-84 | 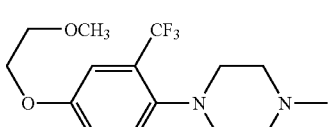 | 572 |
| 1-85 | 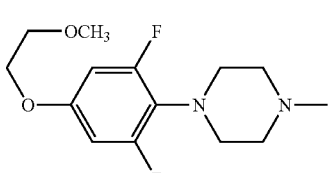 | 540 |
| 1-86 | 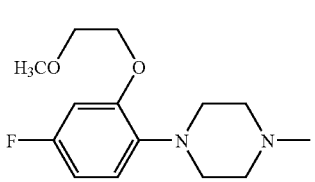 | 522 |

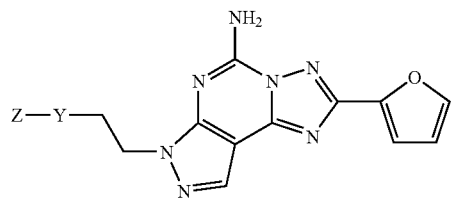
| Example | Z—Y— | MS, [M+1] m/e |
|---|---|---|
| 1-87 | | 518 |
| 1-88 | | 529 |
| 1-89 | | 574 |
| 1-90 | | 572 |
| 1-91 | | 528 |
| 1-92 | | 572 |
| 1-93 | | 529 |
| 1-94 | | 522 |

-continued

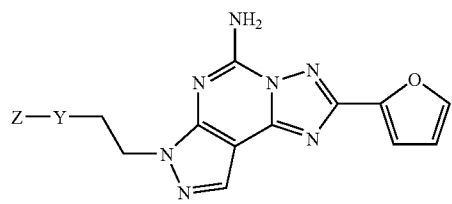

| Example | Z—Y— | MS, [M+1] m/e |
|---|---|---|
| 1-95 | 4-(4-methylpiperazinyl)phenoxy-ethoxy-ethoxymethyl | 548 |
| 1-96 | 4-(4-methylpiperazinyl)phenoxy-(1,3-dimethoxy-2-propyl) | 548 |
| 1-97 | 4-fluorophenoxy-ethyl-N,N-dimethylamino | 437 |
| 1-98 | 4-(4-methylpiperazinyl)phenoxy-ethoxy-ethyl | 518 |
| 1-99 | 4-(4-methylpiperazinyl)phenoxy-CH₂COOCH₂CH₃ | 532 |
| 1-100 | 4-(4-methylpiperazinyl)phenoxy-CH₂COOH | 504 |
| 1-101 | 4-(4-methylpiperazinyl)phenoxy-propyl-OCH₃ | 518 |
| 1-102 | 4-(4-chlorophenyl)-4-hydroxy-1-methylpiperidine | 479, 501 |
| 1-103 | 2-methyl-1,2,3,4-tetrahydroisoquinoline | 401 |

-continued
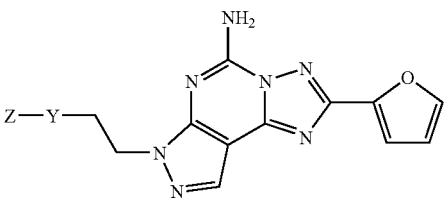
| Example | Z—Y— | MS, [M+1] m/e |
|---|---|---|
| 1-104 | | 454 |
| 1-105 | | 507, 509 |
| 1-106 | | 443 |
| 1-107 | | 471 |
| 1-108 | | 457 |
| 1-109 | | 401 |
| 1-110 | | 440 |
| 1-111 | | 485 |
| 1-112 | | 429 |

-continued
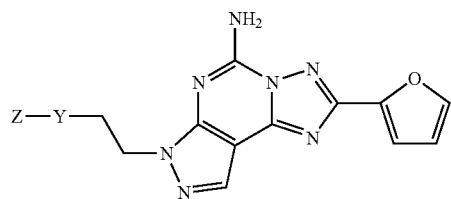
| Example | Z—Y— | MS, [M+1] m/e |
|---|---|---|
| 1-113 | | 499 |
| 1-114 | | 461 |
| 1-115 | | 446 |
| 1-116 | | 475 |
| 1-117 | | 473 |
| 1-118 | | 474 |
| 1-119 | | 458 |
| 1-120 | | 446 |
| 1-121 | | 446 |

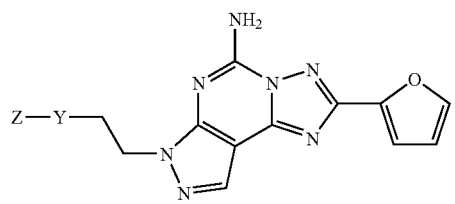

| Example | Z—Y— | MS, [M+1] m/e |
|---|---|---|
| 1-122 | 3,5-dimethoxyphenyl-(4-methylpiperazin-1-yl) | 490 |
| 1-123 | 3,5-dichloro-4-methoxyphenyl-(4-methylpiperazin-1-yl) | 528, 530, 532 |
| 1-124 | 4-methoxyphenyl-(4-methylpiperazin-1-yl) | 460 |
| 1-125 | 3,4-dimethylphenyl-(4-methylpiperazin-1-yl) | 458 |
| 1-126 | 2,4-dimethylphenyl-(4-methylpiperazin-1-yl) | 458 |
| 1-127 | 4-hydroxy-4-phenyl-(1-methylpiperidin-1-yl) | 445 |
| 1-128 | 4-(4-bromophenyl)-4-hydroxy-(1-methylpiperidin-1-yl) | 523, 525 |
| 1-129 | 4-morpholinophenyl-(4-methylpiperazin-1-yl) | 515 |
| 1-130 | 2-methoxypropoxy-phenyl-(4-methylpiperazin-1-yl) | 518 |
| 1-131 | 4-methylsulfonylphenyl-piperazin-1-yl | 493 |

-continued
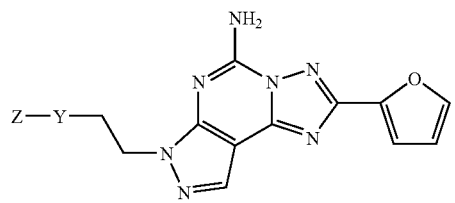
| Example | Z—Y— | MS, [M+1] m/e |
|---|---|---|
| 1-132 | MeO-CH2-CH(OMe)-CH2-O-C6H4-N(piperazine)N-Me | 548 |
| 1-133 | MeO-CH2CH2-O-C6H4-O-CH2CH2-N(Me)Me | 493 |
| 1-134 | (tetrahydropyran-4-yl)-O-C6H4-N(piperazine)N-Me | 530 |
| 1-135 | MeO-S(O)-CH2-O-C6H4-N(piperazine)N-Me | 507 |
| 1-136 | Me-C(O)-CH2-O-C6H4-N(piperazine)N-Me | 487 |
| 1-137 | (2-methoxy-1,3-dioxolan-2-yl)-CH2-O-C6H4-N(piperazine)N-Me | 531 |
| 1-138 | EtOOC-C6H4-N(piperazine)N-Me | 487 |
| 1-139 | Me2N-CH2CH2CH2-O-C6H4-N(piperazine)N-Me | 531 |
| 1-140 | H2NO2S-C6H4-N(piperazine)N-Me | 494 |
| 1-141 | (4-MeO-C6H4)-CH2CH2-NH- | 419 |
| 1-142 | (4-Cl-C6H4)-(1-methyl-tetrahydropyridin-4-yl) | 461, 463 |

-continued

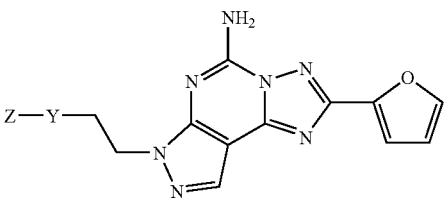

| Example | Z—Y— | MS, [M+1] m/e |
|---|---|---|
| 1-143 |  | 459 |
| 1-144 |  | 441 |
| 1-145 |  | 457 |
| 1-146 |  | 431 |
| 1-147 |  | 407 |

EXAMPLE 2

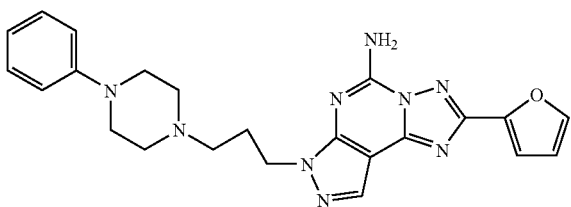

Step 1:

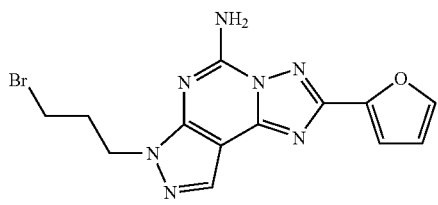

Combine the product of Preparation 1 (0.60 g, 2.5 mmol), 1,3-dibromopropane (0.60 g, 3.0 mmol), and NaH (60% in oil, 0.119 g, 3.0 mmol) in dry DMF (9 ml). Stir under $N_2$ for 2 h, concentrate and flash chromatograph to obtain the title compound as a solid (PMR in $CDCl_3+CD_3OD$: δ 2.43 quint., 3.38+4.51 triplets, 8.09 s), as well as 8-substituted isomer.

Step 2:

Combine the product of Step 1 (0.050 g, 0.14 mmol) and 1-phenylpiperazine (0.045 g, 0.28 mmol) in DMF (2 ml) and heat at 80° C. for 4 h. Concentrate and purify by flash column chromatography ($CH_2Cl_2$, $CH_3OH+NH_3$) to obtain the title compound as a cream solid, mass spectrum m/e=443 (M+H).

Similarly prepare the following compounds:

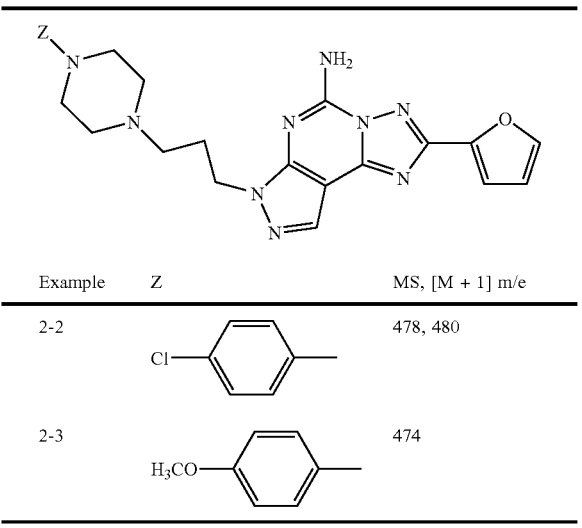

| Example | Z | MS, [M + 1] m/e |
|---|---|---|
| 2-2 | Cl—⟨phenyl⟩— | 478, 480 |
| 2-3 | H₃CO—⟨phenyl⟩— | 474 |

EXAMPLE 3

The compound of Example 1-2 was also prepared by the following procedure:

Combine the product of Preparation 1 (0.15 g, 0.62 mmol), 1-phenyl-4-(2-chloroethyl)piperazine (0.17 g, 0.75 mmol), and NaH (60% in oil, 0.035 g, 0.87 mmol) in dry DMF (7 ml). Stir under $N_2$ for 48 h, add additional chloride (0.03 g) and NaH (0.005 g) and stir another 72 h. Concentrate and purify by flash column chromatography ($CH_2Cl_2$, $CH_3OH+NH_3$) to obtain the title compound as a cream solid, mass spectrum m/e=429 (M+H).

The compound of Example 1-3 is similarly prepared, as are the following compounds:

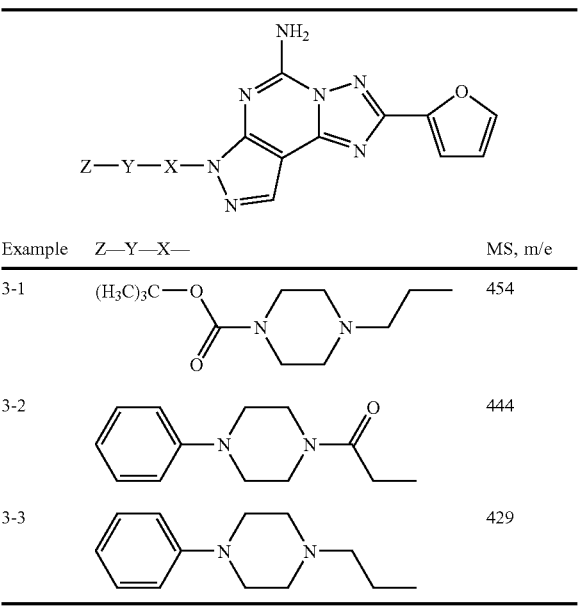

| Example | Z—Y—X— | MS, m/e |
|---|---|---|
| 3-1 | (H₃C)₃C—O—C(O)—N⟨piperazine⟩N—CH₂CH₂— | 454 |
| 3-2 | phenyl—N⟨piperazine⟩N—C(O)—CH₂— | 444 |
| 3-3 | phenyl—N⟨piperazine⟩N—CH₂CH₂— | 429 |

EXAMPLE 4

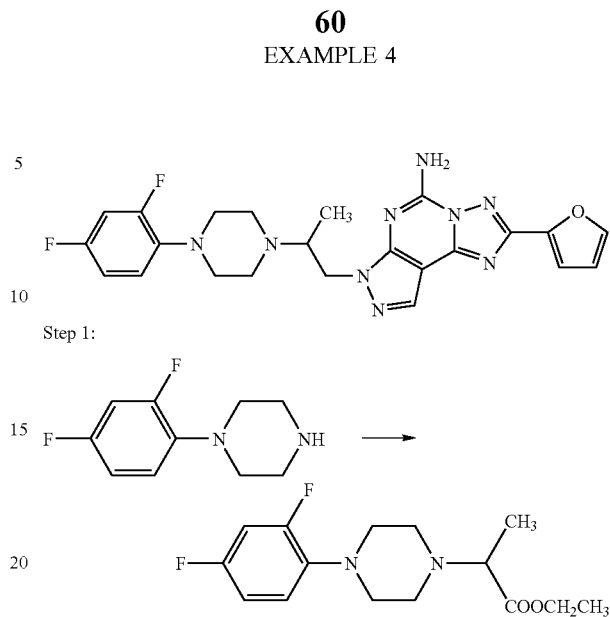

Step 1:

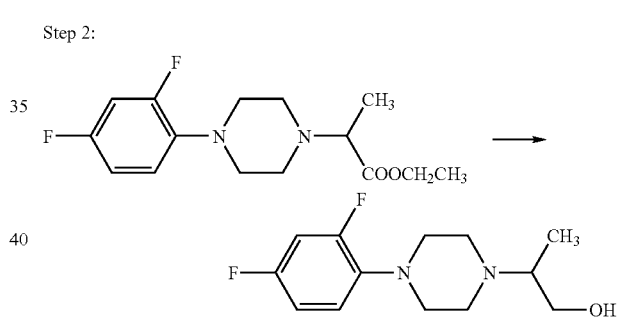

Combine 1-(2,4-difluorophenyl)piperazine (1.5 g, 7.6 mmol), ethyl 2-bromopropionate (1.65 g, 9.1 mmol) and DIPEA (1.1 g, 8.3 mmol) in DMF (8 ml). Stir 4 h, concentrate, and partition between $Et_2O$ and water. Wash with brine, dry ($MgSO_4$), and concentrate to obtain the ester as a yellow oil, NMR ($CDCl_3$) consistent.

Step 2:

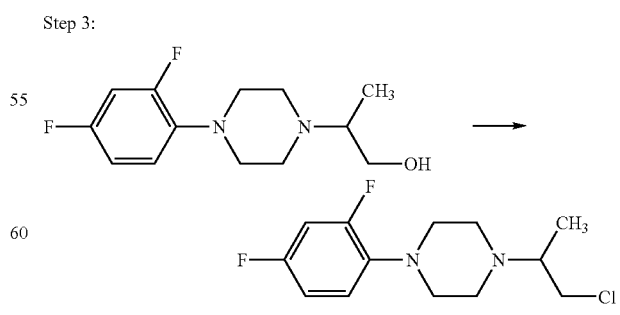

To the product of Step 1 (2.15 g, 7.2 mmol) in THF (10 ml), add $LiAlH_4$ (1.0 M in THF, 4.4 ml, 4.4 mmol) dropwise. Heat at 60° C. 1 h, add water (0.16 ml), 15% NaOH (0.16 ml), and then water (0.49 ml). Filter and concentrate to obtain the alcohol as a yellow oil, NMR ($CDCl_3$) consistent.

Step 3:

To the product of Step 2 (0.90 g, 3.5 mmol) in $CH_2Cl_2$ (10 ml) at 5° C., add $SOCl_2$ (0.38 ml, 5.3 mmol). Allow to warm and stir 16 h. Concentrate and partition between $CH_2Cl_2$ and 1N NaOH, wash with water, dry (MgSO$_4$) and concentrate to obtain the crude product as a yellow oil.

Step 4: Combine the product of Preparation 1 (0.20 g, 0.83 mmol), the product of Step 3 (0.34 g, 1.2 mmol) and NaH (60% in oil, 0.040 g, 1.0 mmol) in dry DMF (5 ml). Heat at 60° C. for 24 h, add additional chloride (0.15 g) and NaH (0.02 g), and heat another 4 h. Concentrate and purify by flash column chromatography (CH$_2$Cl$_2$, CH$_3$OH+NH$_3$) to obtain the title compound as a yellow solid, mass spectrum m/e=479 (M+H).

Similarly, prepare the following:

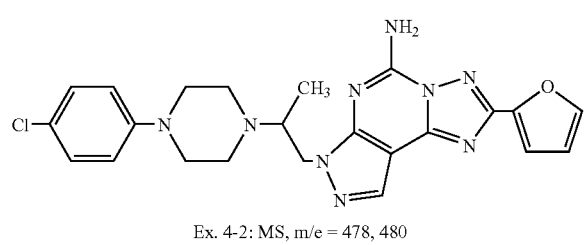

Ex. 4-2: MS, m/e = 478, 480

EXAMPLE 5

Using the procedure of Example 1, substituting the tosylate of Preparation 4 for the tosylate of Preparation 2, prepare the following compounds:

| Ex. | Z | MS, [M + 1] m/e |
|---|---|---|
| 5-1 | 2,4-difluorophenyl | 482 |
| 5-2 | 4-(2-methoxyethoxy)phenyl | 520 |
| 5-3 | 3-fluoro-4-(2-methoxyethoxy)phenyl | 538 |

EXAMPLE 6

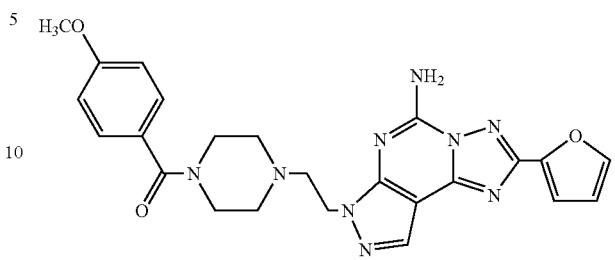

Step 1: To a solution of the product of Example 3-1 (4.17 g, 9.2 mmol) in CH$_2$Cl$_2$ (500 ml), add anhydrous HCl (120 ml of 4.0 M dioxane solution) and stir 2 h. Concentrate to dryness under vacuum and take up the residue in water. Make alkaline with aqueous NaOH and collect the precipitated de-protected product. Mass spectrum: MH+=354.

Step 2: Stir a mixture of the product of Step 1 (71 mg, 0.2 mmol) and 4-methoxy-benzoyl chloride (51 mg, 0.3 mmol) in dry DMF (10 ml) containing N,N-diisopropylethylamine (52 mg, 0.4 mmol) for 6 h at RT. Pour the solution into water and collect the precipitated title compound. Mass spectrum: MH+=488.

In a similar fashion, prepare the following:

| Example | Z— | MS, [M + 1] m/e |
|---|---|---|
| 6-2 | 1,3-benzodioxol-5-ylcarbonyl | 502 |
| 6-3 | acetyl | 396 |
| 6-4 | 3,5-bis(trifluoromethyl)benzoyl | 594 |
| 6-5 | 2-thienylcarbonyl | 464 |

-continued

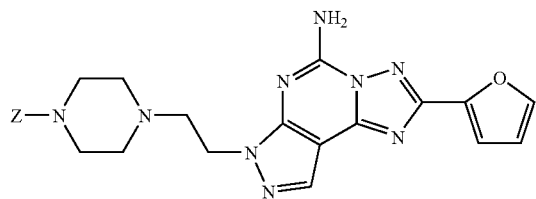

| Example | Z— | MS, [M + 1] m/e |
|---|---|---|
| 6-6 |  | 438 |
| 6-7 | 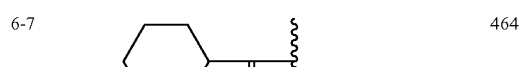 | 464 |
| 6-8 |  | 459 |
| 6-9 | 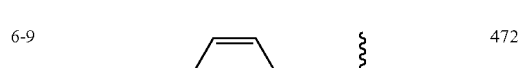 | 472 |
| 6-10 |  | 452 |
| 6-11 | 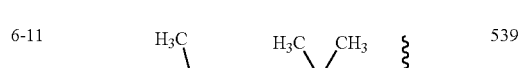 | 539 |
| 6-12 |  | 532 |
| 6-13 | 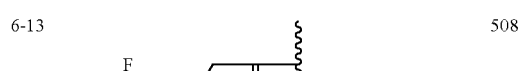 | 508 |

-continued

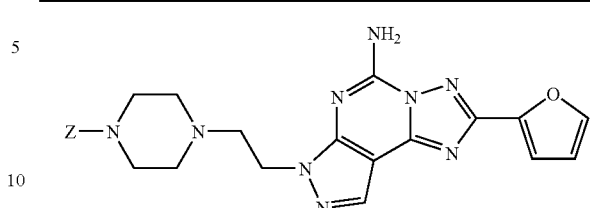

| Example | Z— | MS, [M + 1] m/e |
|---|---|---|
| 6-14 | 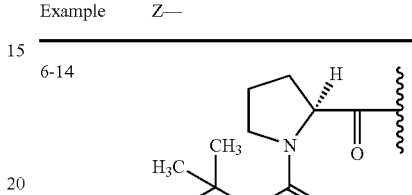 | 551 |
| 6-15 |  | 439 |
| 6-16 | 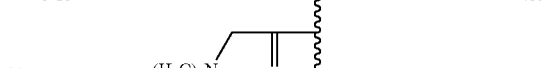 | 492 |

EXAMPLE 7

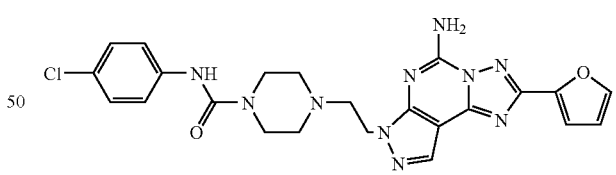

To a solution of the product of Example 6, Step 1 (53 mg, 0.15 mmol) in NMP (10 ml) add 4-chlorophenylisocyanate (25.3 mg, 0.165 mmol) at RT. Stir overnight, add an additional 25.3 mg of the isocyanate, and stir 1 h to complete conversion of all starting material. Pour into water and collect the precipitated title compound. Mass spectrum: MH+=507.

In a similar fashion, prepare the following from the appropriate isocyanate, isothiocyanate or carbamoyl chloride:

EXAMPLE 8

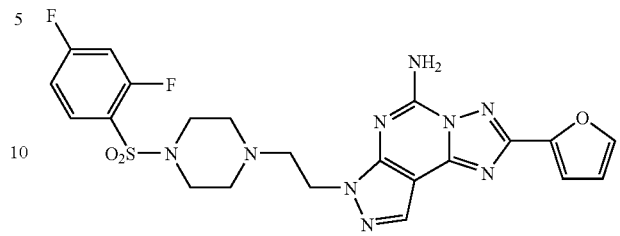

Slurry the product of Example 6, Step 1 (53 mg, 0.15 mmol) in dry DMF (20 ml) containing triethylamine (77 mg, 0.76 mmol); add 2,4-difluorobenzenesulfonyl chloride (37 µl, 0.225 mmol). Stir at RT 2 days. Pour into water and collect the precipitated title compound. Mass spectrum: M+=529.

In a similar fashion, prepare the following:

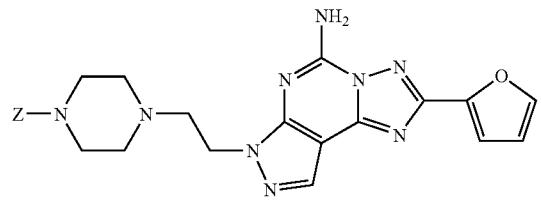

| Example | Z— | MS, [M + 1] m/e |
|---|---|---|
| 7-2 | 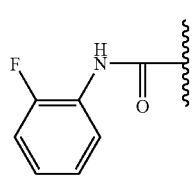 | 517 |
| 7-3 | 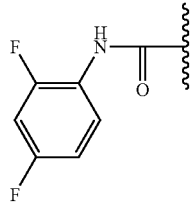 | 451 |
| 7-4 | 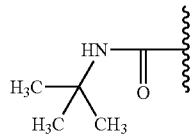 | 453 |
| 7-5 | 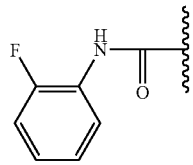 | 491 |
| 7-6 | 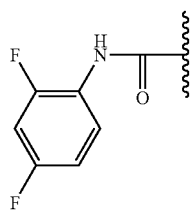 | 509 |
| 7-7 | 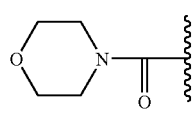 | 467 |

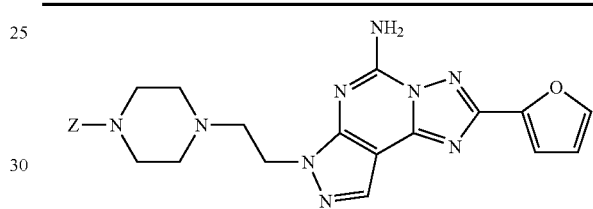

| Example | Z— | MS, [M + 1] m/e |
|---|---|---|
| 8-2 | 2,5-dichlorophenylsulfonyl | 561, 563, 565 |
| 8-3 | 4-methylphenylsulfonyl | 529 |
| 8-4 | 4-bromophenylsulfonyl | 571, 573 |
| 8-5 | 2-fluorophenylsulfonyl | 511 |
| 8-6 | 3,4-dimethoxyphenylsulfonyl | 554 |
| 8-7 | 4-methoxyphenylsulfonyl | 524 |

-continued

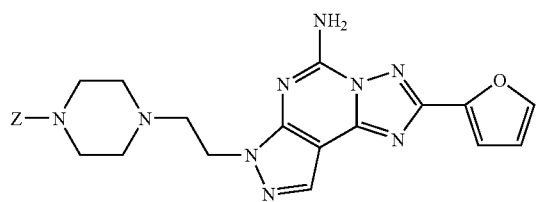

| Example | Z— | MS, [M + 1] m/e |
|---|---|---|
| 8-8 | H₃C—CH₂—S(O)(O)— | 446 |

EXAMPLE 9

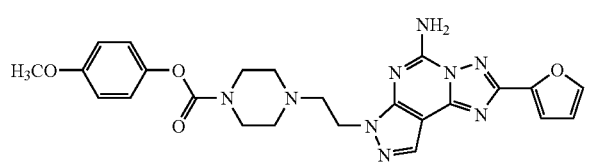

Add 4-methoxyphenyl chloroformate (56 mg, 0.3 mmol) to a slurry of the product of Example 6, Step 1 (71 mg, 0.2 mmol) in warm DMF (25 ml) containing triethylamine (101 mg, 1.0 mmol). Stir the mixture overnight at RT. Concentrate the solution to ⅓ its volume and pour into water. Collect the precipitate, wash with water, and dry in vacuo. Recrystallize from CH₃OH/CH₂Cl₂ to give the title compound. Mass spectrum: MH+=504.

EXAMPLE 10

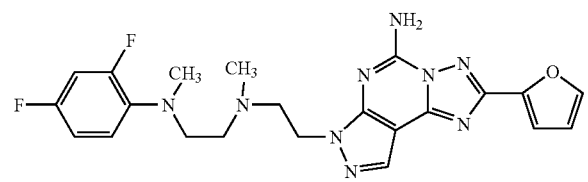

Step 1: Combine 1-bromo-2,4-difluorobenzene (1.00 g, 5.18 mmol), N,N'-dimethyl-ethylenediamine (2.74 g, 31.1 mmol), NaO—t—Bu (0.70 g, 7.2 mmol), Pd(dba)₂ (0.060 g, 0.10 mmol) and (±)-BINAP (0.19 g, 0.31 mmol) in toluene (10 ml). Heat at 110° for 18 h, allow to cool, and extract with 1N HCl. Basify the aqueous solution with NaOH and extract with CH₂Cl₂. Dry, concentrate, and purify by PLC to give N-(2,4-difluoro-phenyl)-N,N'-dimethylethylenediamine.

Step 2: Combine the product of Preparation 2 (0.100 g, 0.23 mmol) with the product of Step 1 (0.091 g, 0.46 mmol) in DMF (2 ml). Heat at 80° for 90 h, allow to cool, concentrate, and purify by column chromatography to obtain the title compound as an oil, mass spec m/e=467.

EXAMPLE 11

The compound of Example 1-2 was also prepared by the following procedure.

Step 1:

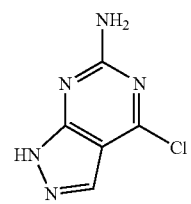

To a solution of the product of Preparation 1, Step 1, (768 mg, 4 mmol) in DMF (20 ml) add N,N-diisopropylethylamine (0.88 ml, 5 mmol), followed by hydrazine hydrate (0.2 ml, 4.1 mmol). The solution warms and a solid precipitates which gradually dissolves over 1 h. After stirring 3 h, concentrate the solution under vacuum to about ⅓ its volume, and pour into water. Collect the precipitate and recrystallize it from CH₃OH to give the chloropyrazolopyrimidine. Mass spectrum: MH+=170.

Step 2:

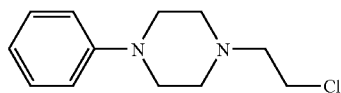

To a stirred solution of 1-phenylpiperazine (6.5 g, 40 mmol) and 50% aqueous chloroacetaldehyde (6.4 ml, 48 mmol) in CH₂Cl₂ (125 ml) at 5–10° C. add, portionwise, Na(OAc)₃BH (12.72 g, 60 mmol). When foaming ceases, allow the mixture to warm to RT and stir for 3 h. Dilute with CH₂Cl₂ (100 ml), and shake with 1N aq NaOH to bring pH above 8. Wash organic layer with water and brine, dry over MgSO₄, and solvent strip. Chromatograph on silica and elute with 1% CH₃OH/CH₂Cl₂ to give the title compound. Mass spectrum: MH+=225.

Step 3:

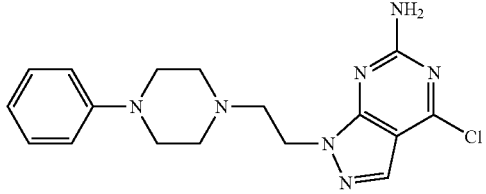

To a slurry of 60% NaH (0.14 g, 3.5 mmol) in DMF (30 ml) at ice bath temperature add, portionwise, the product of Step 1 (0.51 g, 3 mmol). When gas evolution ceases, add the product of Step 2. Stir the resulting mixture at RT overnight. Filter off dark red insoluble matter, and concentrate the filtrate to dryness under vacuum. Triturate the gummy residue with CH₃OH to give the title compound as a light yellow solid. Mass spectrum: MH+=358.

The product of Step 3 was treated as described in Preparation 1, Steps 2 and 4, to obtain the compound of Example 1-2.

EXAMPLE 12

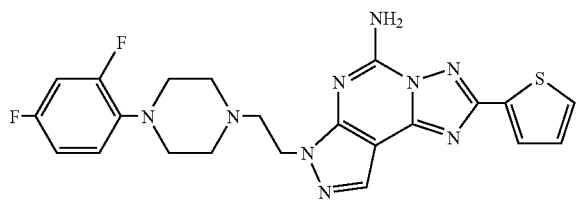

Step 1: To NaH (60% in oil, 142 mg, 3.5 mmol) in DMF (15 ml) add the chloride of Example 11, Step 1 (500 mg, 2.9 mmol). Add to this 1-(2-chloroethyl)-4-(2,4-difluorophenyl)piperazine (846 mg, 3.5 mmol). Stir at RT 90 h and concentrate. Chromatograph to obtain the desired compound as a white solid. PMR in DMSO: δ2.57 (4H, s), 2.76 (2H, t), 2.85 (4H, s), 4.30 (2H, t), 7.0 (2H, m), 7.15 (1H, dxt), 7.26 (2H, s), 7.97(1 H, s).

Step 2: Treat the chloride of Step 1 (37 mg, 0.095 mmol) in DMF (95 ml) with hydrazine hydrate (9.2 µl, 0.19 mmol). After 4 h, concentrate and chromatograph on PLC to obtain the hydrazine as a brown oil. Mass spectrum: MH+=390.

Step 3: Treat the hydrazine from Step 2 (18 mg, 0.047 mmol) in DMF (2 ml) with thiophene-2-carbonyl chloride (5.2 µl, 0.047 mmol) and DIPEA (12.2 µl, 0.07 mmol). After 4 h, concentrate and chromatograph on PLC to obtain the hydrazide as a yellow oil. Mass spectrum: MH+=500.

Step 4: Heat the hydrazide from Step 3 (13 mg, 0.026 mmol) in N,O-bis(trimethyl-silyl)acetamide (1 ml) for 2 h at 100° C. Concentrate and chromatograph on PLC to obtain the title compound as a white solid. Mass spectrum: MH+=482.

The 1-(2-chloroethyl)-4-(2,4-difluorophenyl)piperazine employed in this sequence is prepared in two steps. Add chloroacetyl chloride (1.76 ml, 22.1 mmol) and N-methyl-morpholine (2.65 ml, 24.1 mmol) to 1-(2,4-difluorophenyl)piperazine (3.98 g, 20.1 mmol) in $CH_2Cl_2$ (15 ml) at 0° C. Stir at RT 1 h, concentrate, partition EtOAc-water, dry, and concentrate to obtain the amide as a brown oil. To a 0° C. solution of this (4.71 g, 17.1 mmol) in THF (25 ml) add dropwise $BH_3.CH_3S$/THF (2M, 12.8 ml, 25.6 mmol). Stir at RT overnight, quench with $CH_3OH$, concentrate, and partition with $CH_2Cl_2$-water. Dry and concentrate the organic layer. Treat the crude product a second time with $BH_3.CH_3S$/THF and work up as above to provide the chloroethylpiperazine as a brown oil.

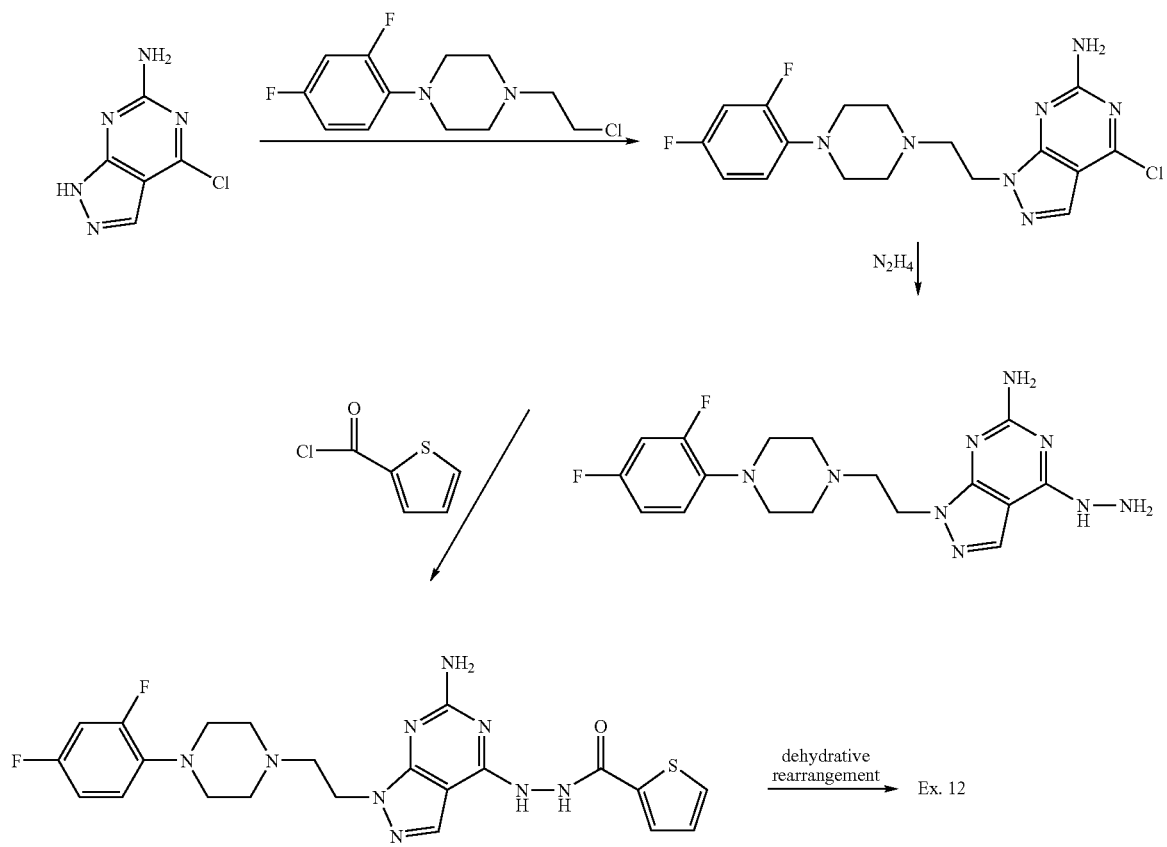

EXAMPLE 13

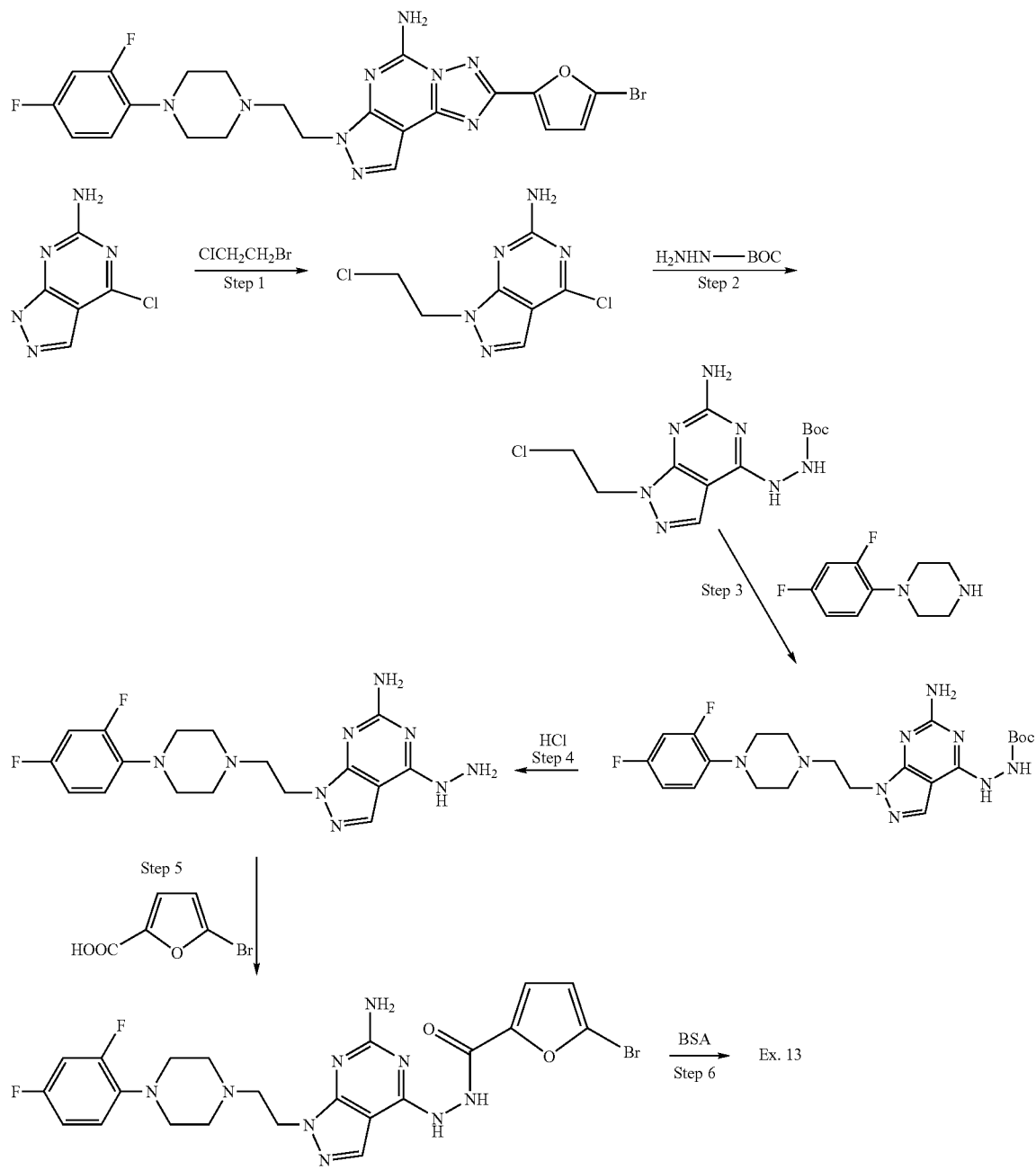

Step 1: To NaH (2.14 g, 60% in oil, 53 mmol) in DMF (20 ml), add the product of Example 11, Step 1 (7.55 g, 45 mmol). Add 1-bromo-2-chloroethane (14.8 ml, 178 mmol). Stir 1.5 h and concentrate. Chromatograph to give the dichloride as a white solid.

Step 2: To the product of Step 1 (3.7 g, 16 mmol) in DMF (20 ml) add t-butyl carbazate (2.53 g, 19 mmole). Heat at 80° C. for 18 h and concentrate. Chromatograph to obtain the carbazate as a white solid.

Step 3: To the product of Step 2 (3.16 g, 9.6 mmol) and KI (1.6 g, 9.6 mmol) in DMF (25 ml) add 1-(2,4-difluorophenyl)piperazine (3.82 g, 19 mmol). Heat at 90° C. for 68 h and concentrate. Chromatograph to obtain the piperazine as a brown solid.

Step 4: Dissolve the product of Step 3 (3.38 g, 6.9 mmol) in 1:1 CH$_3$OH—CH$_2$Cl$_2$ (50 ml). Add 4M HCl in dioxane (20 ml). Stir 16 h and add aq. NH$_3$ to pH 11–12. Concentrate and chromatograph to obtain the hydrazine as a yellow solid.

Step 5: Combine the product of Step 4 (0.120 g, 0.31 mmol) with 5-bromo-2-furoic acid (0.071 g, 0.37 mmol) and HOBt.H$_2$O (0.050 g, 0.37 mmol) in DMF (6 ml). Add EDCl (0.071 g, 0.37 mmol) and stir 1 h. Concentrate and chromatograph to obtain the hydrazide as a yellow solid.

Step 6: Dissolve the product of Step 5 (0.163 g, 0.28 mmol) in N,O-bis(trimethylsilyl) acetamide (6 ml). Heat at 120° C. for 16 h and pour into $CH_3OH$. Concentrate and chromatograph to obtain the title product as an off-white solid: MS m/e 544+546 (M+1).

Similarly prepare compounds of the following structure, wherein R is as defined in the table:

| Example | R | MS m/e |
|---|---|---|
| 13-2 | Me-furan | 480 |
| 13-3 | Cl-furan | 500, 502 |
| 13-4 | pyrrole-NH | 465 |
| 13-5 | N-Me pyrrole | 479 |
| 13-6 | Br-furan | 544, 546 |
| 13-7 | cyclopentenyl | 466 |
| 13-8 | 3,5-difluorophenyl | 512 |
| 13-9 | phenyl | 476 |
| 13-10 | F-furan | 484 |

EXAMPLE 14

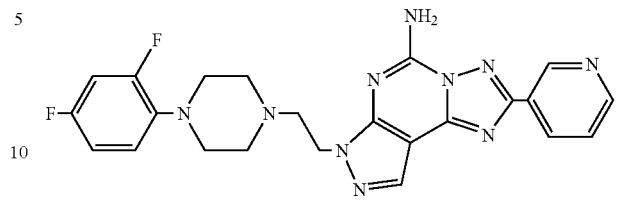

Treat the product of Example 13, Step 4 (0.080 g, 0.20 mmol) with nicotinoyl chloride hydrochloride (0.044 g, 0.25 mmol) and diisopropylethylamine (0.086 ml, 0.49 mmol) in DMF (4 ml). Stir 2 h, concentrate and chromatograph to obtain the hydrazide as a white solid.

Treat this material with BSA as in Example 13, Step 6 to obtain the title compound as a white solid: MS m/e 477 (M+1).

Similarly prepare compounds of the following structure, wherein R is as defined in the table:

| Example | R | MS, m/e |
|---|---|---|
| 14-2 | furan-$NO_2$ | 511 |
| 14-3 | F-phenyl | 494 |

EXAMPLE 15

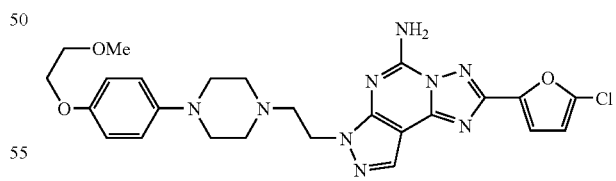

Step 1: To the product of Example 13, Step 2 (3.54 g, 10.8 mmol) and KI (1.79 g, 10.8 mmol) in DMF (35 ml) add 1-(4-(2-methoxyethoxy)phenyl)piperazine (5.1 g, 22 mmol). Heat at 90° C. for 90 h and concentrate. Chromatograph to obtain the piperazine as a brown solid.

Step 2: Treat the product of Step 1 with HCl as in Example 13, Step 4, to obtain the hydrazine as a yellow solid.

Step 3: Treat the product of Step 2 with 5-chloro-2-furoic acid as in Example 13, Step 5, to obtain the hydrazide as a yellow solid.

Step 4: Treat the product of Step 3 with BSA as in Example 13, Step 6. Chromatograph to obtain the title compound as a white solid, MS m/e 538+540 (M+1).

Similarly prepare compounds of the following structure, wherein R is as defined in the table:

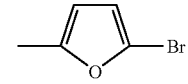

| Example | R | MS, m/e |
|---|---|---|
| 15-2 | 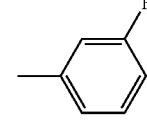 | 582, 584 |
| 15-3 | 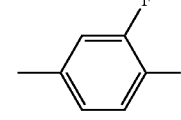 | 532 |
| 15-4 | 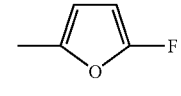 | 550 |
| 15-5 | 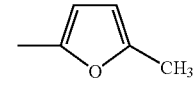 | 522 |
| 15-6 | 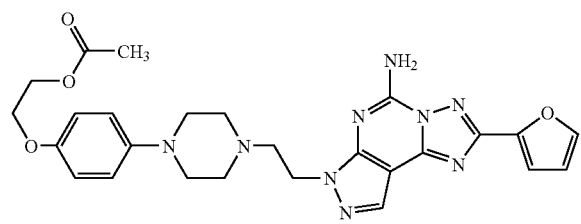 | 518 |

EXAMPLE 16

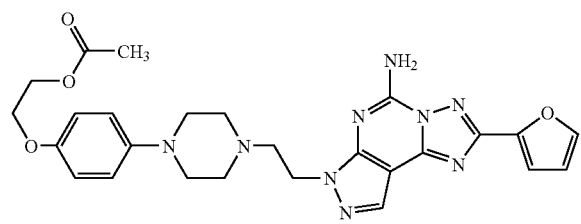

Combine the product of Example 1-83 (0.080 g, 0.16 mmol) with Ac$_2$O (0.028 ml, 0.28 mmol) and 4-dimethylaminopyridine (0.004 g, 0.03 mmol) in DMF (5 ml). Stir 4 h, concentrate, and chromatograph to obtain the acetate ester as a white solid, MS: m/e=532 (M+1).

EXAMPLE 17

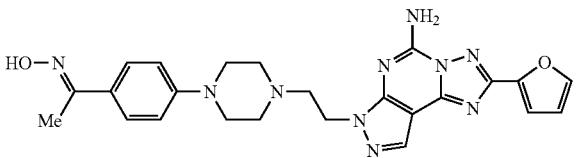

Combine the product of Example 1-21 (0.100 g, 0.21 mmol) with H$_2$NHOH·HCl 0.029 g, 0.42 mmol) in 95% EtOH (9 ml). Add 10 drops conc. HCl, heat at reflux 5 h, add DMF (1.5 ml), heat 18 h, allow to cool, and filter to obtain the oxime as a white solid, MS: m/e=487 (M+1). Chromatograph the mother liquor to obtain additional product.

Similarly prepare the methoxime, a white solid, MS: m/e=501 (M+1):

Ex. 17-2

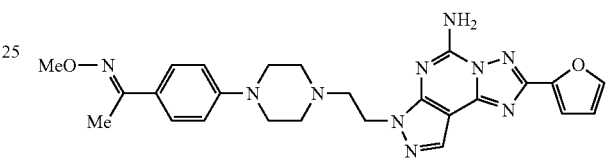

EXAMPLE 18

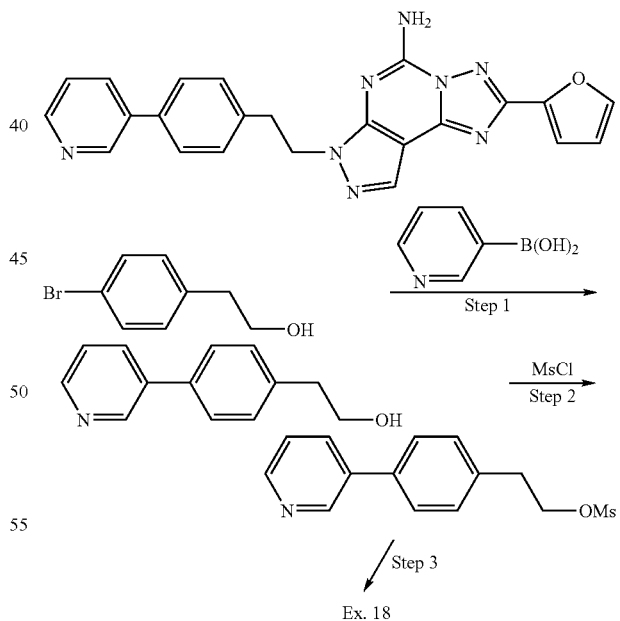

Step 1: To a solution of 4-bromophenethyl alcohol (0.600 g, 2.98 mmol) and 3-pyridinylboronic acid (0.734 g, 5.97 mmol) in toluene (35 ml) and EtOH (9 ml), add a solution of K$_2$CO$_3$ (0.8826 g, 5.97 mmol) in H$_2$O (16 ml) and tetrakis(triphenyl-phosphine)palladium(0) (0.172 g, 0.149 mmol). Heat in a sealed tube 18 h at 120° C. and cool. Extract with EtOAc, wash with brine, dry (K$_2$CO$_3$)

and concentrate. Chromatograph on silica (30–50% EtOAc/hexanes) to obtain the biaryl alcohol.

Step 2: To the product of Step 1 (0.540 g, 2.71 mmol) in CH$_2$Cl$_2$ (15 ml) at 0° C. add mesyl chloride (0.35 ml, 3.52 mmol) and Et$_3$N (0.57 ml, 4.00 mmol). Stir 2.5 h and extract with CH$_2$Cl$_2$. Dry (Na$_2$SO$_4$) and concentrate to obtain the mesylate.

Step 3: Add the product of Preparation 4 (0.347 g, 1.44 mmol) to the mesylate of Step 2 (0.480 g, 1.73 mmol) in DMF (4.5 ml), followed by NaH (60% in oil, 0.082 g, 4.04 mmol). Stir 18 h and extract with EtOAc. Wash with H$_2$O, dry (K$_2$CO$_3$) and concentrate. Purify by PTLC (5% CH$_3$OH/CH$_2$Cl$_2$, developed twice) to obtain the title compound as a white solid, MS: 423 (M+1).

By the above method, prepare the following (Example 18-8 from commercial biphenylethanol):

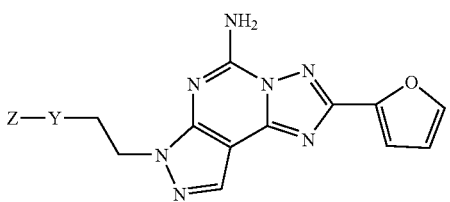

| Example | Z—Y— | MS, m/e |
|---|---|---|
| 18-2 | MeS-⌬-⌬- | 468 |
| 18-3 | MeO-⌬-⌬- | 452 |
| 18-4 | EtO-⌬-⌬- | 466 |
| 18-5 | F$_3$CO-⌬-⌬- | 506 |
| 18-6 | MeO-(pyridyl)-⌬- | 453 |
| 18-7 | (4-pyridyl)-⌬- | 423 |
| 18-8 | ⌬-⌬- | 422 |
| 18-9 | (3-pyridyl)-⌬- | 423 |

EXAMPLE 19

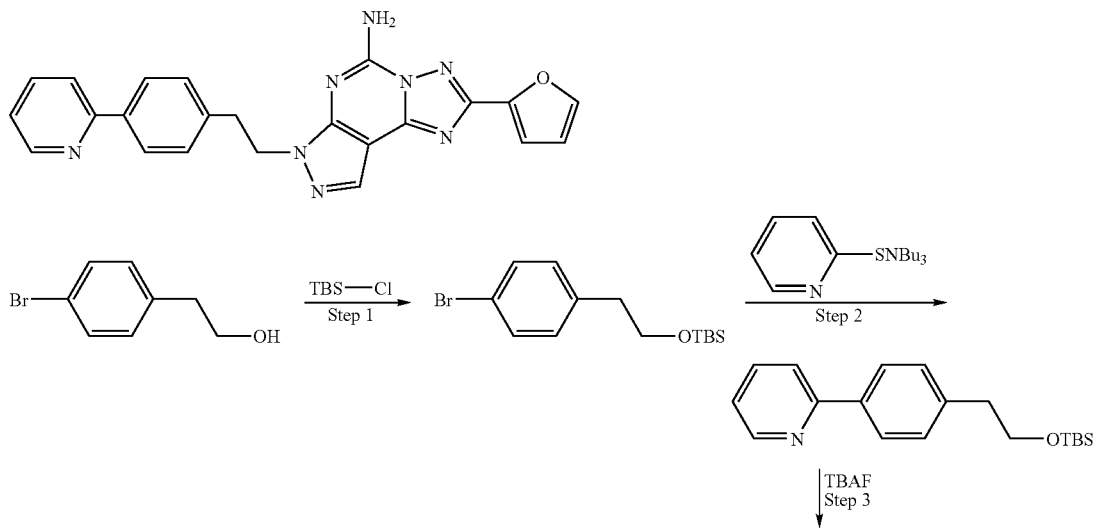

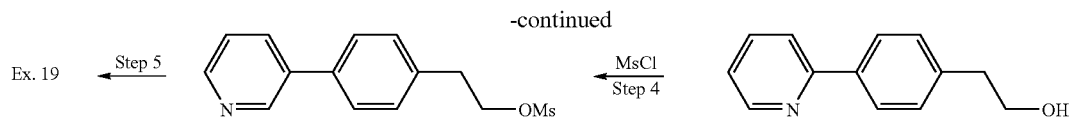

Step 1: Combine 4-bromophenethyl alcohol (3.00 g, 14.9 mmol), triethylamine (2.68 ml, 19.2 mmol), dimethylaminopyridine (0.180 g, 1.47 mmol) and t-butyldimethylsilyl chloride (2.45 g, 16.3 mmol) in $CH_2Cl_2$ (75 ml). Stir 1 h, wash with $H_2O$, dry ($K_2CO_3$), and concentrate. Chromatograph on silica (hexanes) to obtain the silyl ether.

Step 2: To the compound of Step 1 (0.300 g, 0.95 mmol) in dry toluene (15 ml) add 2-(tri-butylstannyl)pyridine (1.05 g, 2.86 mmol) and tetrakis(triphenylphosphine)-palladium (0.11 g, 0.095 mmol). Flush with $N_2$ and heat 16 h at 120° C. Cool, filter through Celite, and wash with $NH_4Cl$, brine and then water. Dry ($K_2CO_3$) and concentrate. Chromatograph on silica (3–5% EtOAc/hexanes) to obtain the biaryl, MS 314 (M+1).

Step 3: Combine the biaryl of Step 2 (0.180 g, 0.57 mmol) and TBAF (1.0 M in THF, 1.7 ml) in THF (5.7 ml). Stir 2 h, wash with saturated $NH_4Cl$, and extract with EtOAc. Wash with $H_2O$ several times, dry ($K_2CO_3$) and concentrate to obtain the alcohol.

Steps 4 and 5: Conduct as in Example 18, Steps 2 and 3, to obtain the title compound as a white solid, MS: 423 (M+1).

Similarly prepare the following compounds:

Ex. 19-2, MS: 424 (M+1)

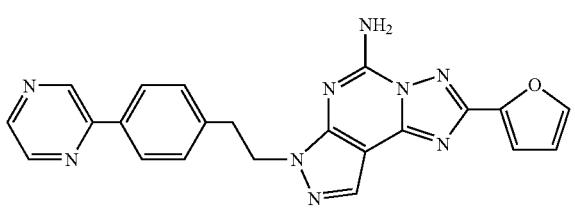

Ex. 19-3, MS: 423 (M+1)

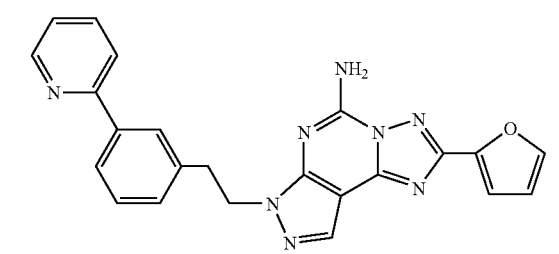

EXAMPLE 20

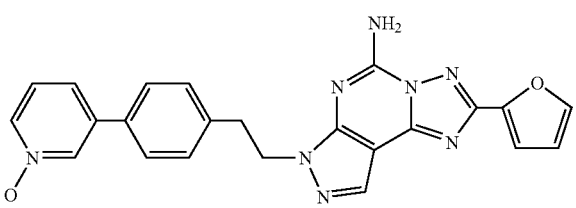

To the product of Example 18 (0.055 g, 0.13 mmol) in $CH_2Cl_2$ (1.5 ml) at −78° C. add m-CPBA (0.050 g, 0.29 mmol). Allow to warm, stir 5 h, and wash successively with sat. $Na_2S_2O_3$, 5% $K_2CO_3$, and $H_2O$. Dry ($Na_2SO_4$) and concentrate. Purify by PTLC (10% $CH_3OH/CH_2Cl_2$) to obtain the title compound, MS: 439 (M+1).

Similarly, oxidize the product of Example 18-2 at 0° C. or RT to produce the sulfoxide, MS: 484 (M+1), or the sulfone, MS: 500 (M+1).

Ex. 20-2

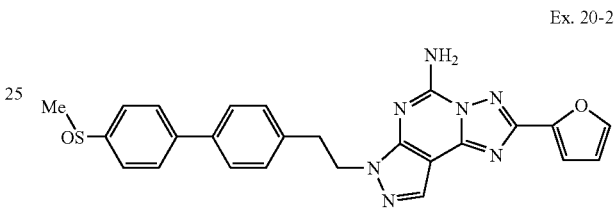

Ex. 20-3

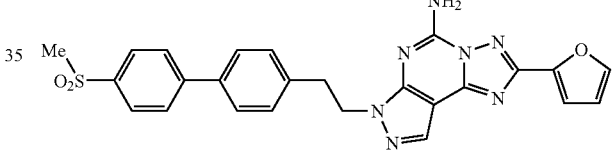

EXAMPLE 21

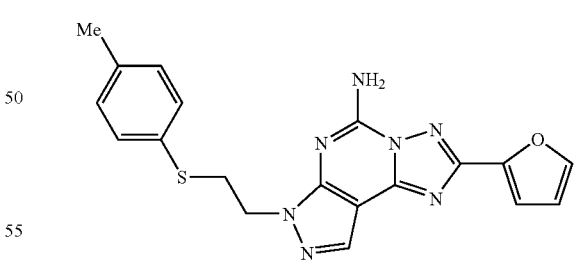

Combine the product of Preparation 6 (0.104 g, 0.30 mmol), 4-methyl-benzenethiol (0.075 g, 0.60 mmol), and $K_2CO_3$ (0.091 g, 0.66 mmol) in DMF (20 ml). Heat at 80° C. for 5 h and concentrate. Partition between EtOAc and water, wash with brine, dry over $MgSO_4$ and concentrate. Recrystallize from $CH_3OH$ to obtain the title compound, MS: m/e=392 (M+1).

Similarly prepare the following compounds:

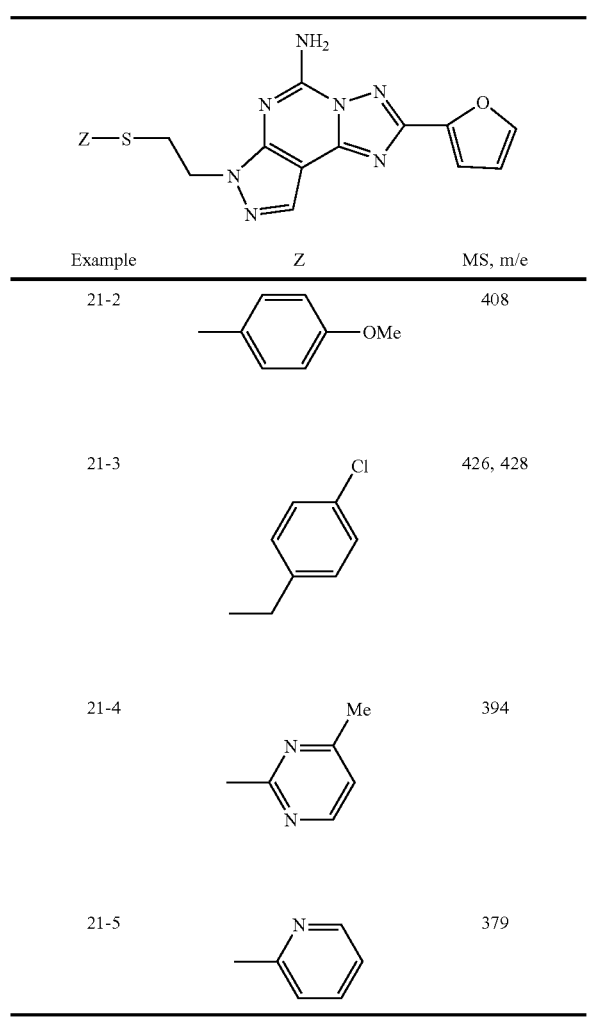

| Example | Z | MS, m/e |
|---|---|---|
| 21-2 | –C₆H₄–OMe (4-methoxyphenyl) | 408 |
| 21-3 | 4-chlorobenzyl | 426, 428 |
| 21-4 | 2-methyl-4-methylpyrimidinyl | 394 |
| 21-5 | 2-pyridylmethyl | 379 |

EXAMPLE 22

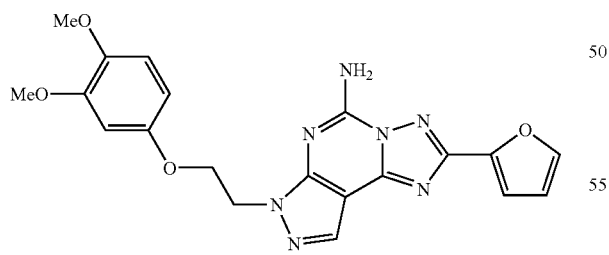

Combine the product of Preparation 6 (0.11 g, 0.25 mmol), 3,4-dimethoxy-phenol (0.154 g, 1.0 mmol), and $K_2CO_3$ (0.138 g, 1.0 mmol) in DMF (5 ml). Heat at 90° C. for 48 h and concentrate. Partition between EtOAc and water, wash with 1N NaOH and then brine, dry over $MgSO_4$, and concentrate. Chromatograph on silica (1.5% $CH_3OH$/ $CH_2Cl_2$) to obtain the title compound, MS: m/e=422 (M+1).

Similarly prepare the following compound, MS: m/e=454 (M+1).

Ex. 22-2

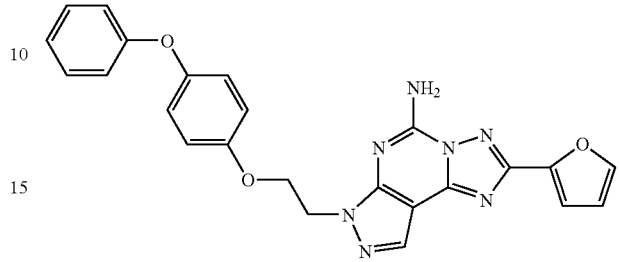

EXAMPLE 23

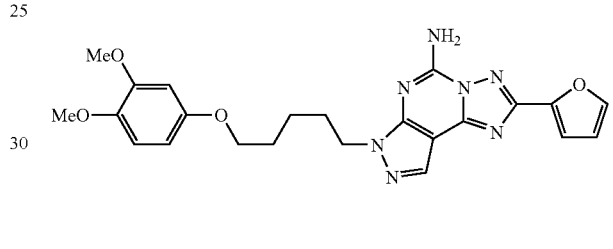

Step 1: To NaH (60% in oil, 1.32 g, 33 mmol) in DMF (25 ml) at 5° C. add dropwise, with stirring, 3,4-dimethoxyphenol (4.77 g, 30 mmol). After 0.5 h, add 1,5-dibromopentane (20.7 g, 90 mmol). Stir 2 h and concentrate. Chromatograph on silica ($CH_2Cl_2$) to obtain the monobromide, MS: m/e=303 (M+1).

Step 2: To NaH (60% in oil, 0.044 g, 1.1 mmol) in DMF (25 ml) at 5° C. add the product of Preparation 1 (0.241 g, 1.1 mmol). After 0.5 h, add the compound from Step 1. Allow to warm, stir 18 h, and concentrate. Partition between EtOAc and water, wash with 1N NaOH and then brine, dry over $MgSO_4$, and concentrate. Chromatograph on silica (2% $CH_3OH/CH_2Cl_2$) and recrystallize the appropriate fraction from $CH_3CN$ to obtain the title compound, MS: m/e=464 (M+1).

EXAMPLE 24

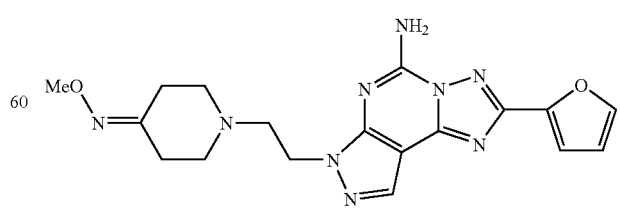

EXAMPLE 25

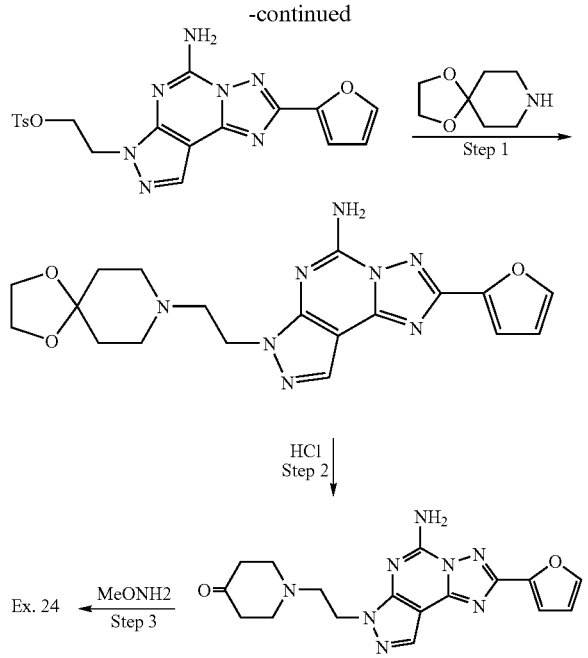

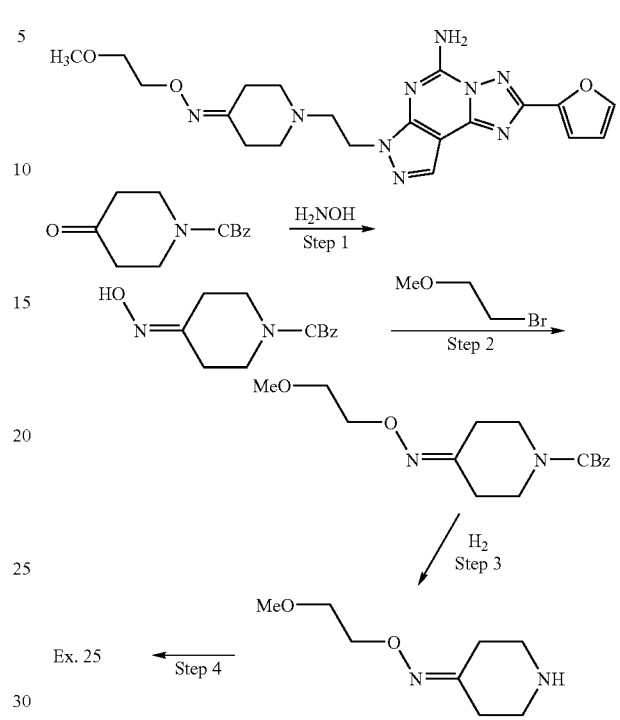

Step 1: Combine 1,4-dioxa-8-azaspiro(4,5)decane (0.48 ml, 3.8 mmol) with the product of Preparation 2 (0.66 g, 1.5 mmol) in DMF (10 ml). Heat at 90° C. for 16 h, allow to cool, filter and wash with CH₃OH to give off-white solid, MS: m/e 411 (M+1).

Step 2: Heat the product of Step 1 (0.476 g, 1.16 mmol) in acetone (10 ml) and 5% HCl (10 ml) at 100° C. for 16 h. Cool, neutralize with sat. NaHCO₃, and extract with 10% CH₃OH in CH₂Cl₂. Dry (MgSO₄), concentrate and chromatograph on silica with CH₃OH—CH₂Cl₂ to obtain the ketone as a white powder, MS: m/e 367 (M+1).

Step 3: Combine the product of Step 2 (0.050 g, 0.13 mmol) with O-methylhydroxyl-amine hydrochloride (0.033 g, 0.39 mmol) in pyridine (3 ml). Stir for 16 h and concentrate. Partition between NaHCO₃ (sat.) and 5% CH₃OH in CH₂Cl₂. Dry (MgSO₄), concentrate and chromatograph on silica with 5% CH₃OH—CH₂Cl₂ to obtain the title compound as a white solid, MS: m/e 396 (M+1).

Similarly prepare the following compounds:

| Example | R¹¹ | MS, m/e |
|---|---|---|
| 24-2 | —CH₂CH₃ | 410 |
| 24-3 | —CH₂CH₂CH₃ | 424 |
| 24-4 | —CH₂CHCH₂ | 422 |
| 24-5 | —C(CH₃)₃ | 438 |
| 24-3 | —C₆H₅ | 458 |
| 24-4 | —CH₂C₆H₅ | 472 |

Step 1: Combine benzyl 4-oxo-1-piperidinecarboxylate (1.0 g, 4.3 mmol) with H₂NOH.HCl (0.89 g, 13 mmol) in pyridine (5 ml). Stir 16 h and concentrate. Partition between NaHCO₃ (sat.) and EtOAc, dry (MgSO₄) and concentrate to give the oxime.

Step 2: Combine the product of Step 1 (0.44 g, 1.8 mmol) with 2-bromoethyl methyl ether (0.20 ml, 2.2 mmol) and NaH (0.10 g, 2.7 mmol) in DMF (8 ml). Stir 16 h and concentrate. Partition between NH₄Cl (sat.) and ether, dry (MgSO₄), and concentrate. Chromatograph the residue on silica with 20% EtOAc-hexane to obtain the alkylated oxime.

Step 3: Stir the product of Step 2 (0.45 g, 1.47 mmol) over 5% Pd/C (0.045 g) in EtOAc (25 ml) under H₂ for 6 h. Filter and concentrate to obtain the amine.

Step 4: Treat the amine of Step 3 with the product of Preparation 2 as in Example 24, Step 1, to obtain the title compound as a white solid, MS: m/e 440 (M+1).

EXAMPLE 26

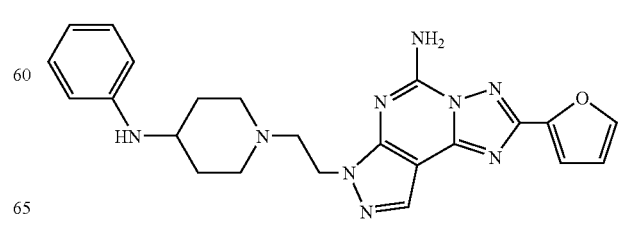

Add sodium triacetoxyborohydride (0.083 g, 0.39 mmol) to a mixture of the product of Example 24, Step 2 (0.050 g, 0.13 mmol), aniline (0.035 ml, 0.39 mmol), and AcOH (0.045 ml, 0.78 mmol) in dichloroethane (3 ml). Stir 16 h and partition between NaHCO$_3$ (sat.) and 5% CH$_3$OH in CH$_2$Cl$_2$. Dry (MgSO$_4$) and concentrate. Chromatograph (5% CH$_3$OH—CH$_2$Cl$_2$) to obtain the title compound as a white solid, MS: m/e 444 (M+1).

In similar fashion, prepare the following compound, MS: m/e 445 (M+1).

Ex. 26-2

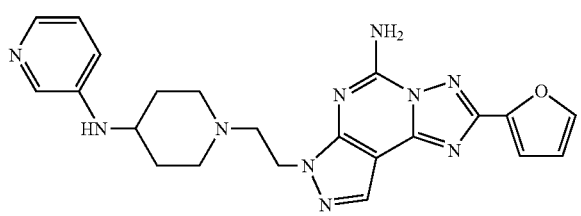

EXAMPLE 27

Step 1: Combine 4-bromophenol (3.46 g, 20.0 mmol) with 2-bromoethyl methyl ether (2.82 ml, 30.0 mmol) and K$_2$CO$_3$ (8.30 g, 60.0 mmol) in acetone (50 ml). Heat at reflux 16 h, cool, filter, and concentrate. Chromatograph on silica with 5% EtOAc/hexane to give the ether as a clear oil. To this ether (2.73 g, 11.8 mmol) in dry THF (50 ml) at −78° C. add n-BuLi (1.6 M in hexane, 7.4 ml, 11.8 mmol). Stir for 10 min. and add a solution of benzyl 4-oxo-1-piperidinecarboxylate (2.5 g, 10.7 mmol) in dry THF (5 ml). Stir for 2 h and allow to warm. Partition between sat. NH$_4$Cl and EtOAc, dry (MgSO$_4$) and concentrate. Chromatograph on silica with EtOAc/hexane (20:80, then 40:60) to obtain the alcohol.

Step 2: To a solution of the product of Step 1 (0.386 g, 1.0 mmol) and triethylsilane (0.80 ml, 5.0 mmol) in dry CH$_2$Cl$_2$ (10 ml) at −78° C. add trifluoroacetic acid (0.38 ml, 5.0 mmol). Allow to warm over 2 h and partition between sat. NaHCO$_3$ and CH$_2$Cl$_2$. Dry (MgSO$_4$) and concentrate. Chromatograph on silica with 20% EtOAc/hexane to obtain the reduction product, MS: m/e 370 (M+1).

Step 3: Stir the product of Step 2 (0.300 g, 0.758 mmol) over 5% Pd/C (0.030 g) in EtOAc (5 ml) and CH$_3$OH (5 ml) under H$_2$ for 2 h. Filter and concentrate to obtain the amine.

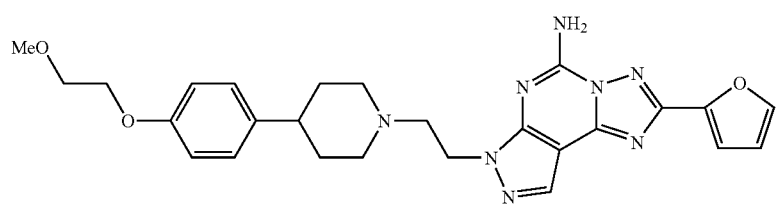

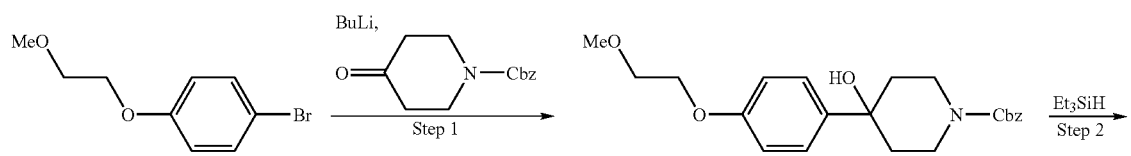

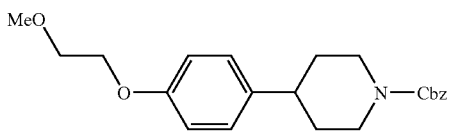

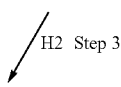

  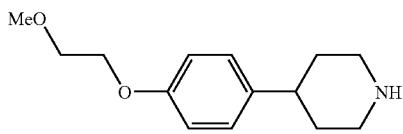

Step 4: Treat the amine of Step 3 with the product of Preparation 2 as in Example 24, Step 1, to obtain the title compound as a white solid, MS: m/e 503 (M+1).

EXAMPLE 28

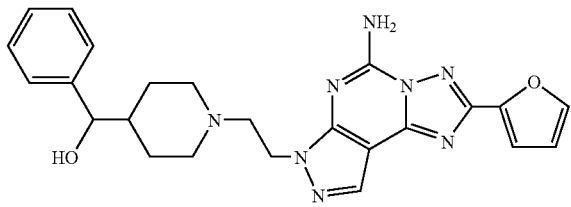

Treat the product of Example 1-145 (0.020 g, 0.044 mmol) in EtOH (0.5 ml) at 0° C. with sodium borohydride (0.005 g, 0.13 mmol) and with an equal amount again after 0.75 h. After another 0.75 h, partition between $CH_2Cl_2$ and sat. $NH_4Cl$. Dry ($Na_2SO_4$) and concentrate. Purify by PTLC (10% $CH_3OH/CH_2Cl_2$) to obtain the title compound as a white solid, MS: 459 (M+1).

EXAMPLE 29

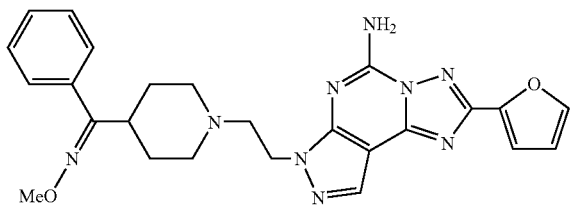

Treat the product of Example 1-145 (0.020 g, 0.044 mmol) in pyridine (0.5 ml) with methoxyamine hydrochloride (0.011 g, 0.13 mmol). Stir 16 h and concentrate. Partition between $CH_2Cl_2$ and sat. $NaHCO_3$. Dry ($Na_2SO_4$) and concentrate. Purify by PTLC (5% $CH_3OH/CH_2Cl_2$) to obtain the title compound as a white solid, MS: 486 (M+1).

Similarly, prepare the oxime 29-2 as two separated geometric isomers, each a white solid, MS: 472 (M+1).

Ex. 29-2

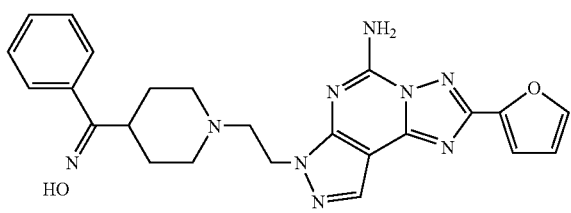

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, and psychoses of organic origin. In particular, the compounds of the present invention can improve motor-impairment due to neurodegenerative diseases such as Parkinson's disease.

The other agents known to be useful in the treatment of Parkinson's disease which can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone. One to three other agents can be used in combination with the compounds of formula I, preferably one.

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 μM NECA (RBI, Natick, Mass.). Working stock is prepared at 400 μM in compound dilution buffer.

Compound Dilution:

Prepare 1 mM stock solutions of compounds in 100% DMSO. Dilute in compound dilution buffer. Test at 10 concentrations ranging from 3 μM to 30 pM. Prepare working solutions at 4× final concentration in compound dilution buffer.

Assay Procedure:

Perform assays in deep well 96 well plates. Total assay volume is 200 μl. Add 50 μl compound dilution buffer (total ligand binding) or 50 μl CGS 15923 working solution ($A_{2a}$ non-specific binding) or 50 μl NECA working solution ($A_1$ non-specific binding) or 50 μl of drug working solution. Add 50 μl ligand stock ([3H]-SCH 58261 for $A_{2a}$, [3H]-DPCPX for $A_1$). Add 100 μl of diluted membranes containing the appropriate receptor. Mix. Incubate at room temperature for 90 minutes. Harvest using a Brandel cell harvester onto Packard GF/B filter plates. Add 45 μl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175–200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275–300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 1971, 6-OHDA and Cathecolamine Neurons, North Holland, Amsterdam, 101–127), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 μg 6-OHDA-HCl is dissolved in 4 μl of saline with 0.05% ascorbic acid as antioxidant, and infused at the constant flow rate of 1 μl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki vaules of 0.3 to 57 nM, with preferred compounds showing Ki values between 0.3 and 5.0 nM.

Selectivity is determined by dividing Ki for A1 receptor by Ki for A2a receptor. Preferred compounds of the invention have a selectivity ranging from about 100 to about 2000.

Preferred compounds showed a 50–75% decrease in descent latency when tested orally at 1 mg/kg for anticataleptic activity in rats.

In the 6-OHDA lesion test, rats dosed orally with 1 mg/kg of the preferred compounds performed 170–440 turns in the two-hour assay period.

In the haloperidol-induced catalepsy test, a combination of sub-threshold amount of a compound of formula I and a sub-threshold amount of L-DOPA showed a significant inhibition of the catalepsy, indicating a synergistic effect. In the 6-OHDA lesion test, test animals administered a combination of a compound of formula I and a sub-threshold amount of L-DOPA demonstrated significantly higher contralateral turning.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease. The compounds are non-toxic when administered within this dosage range.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of formula I and a dopaminergic agent is administered, lower doses of the components will be effective compared to the doses of the components administered as monotherapy.

The following are examples of pharmaceutical dosage forms which contain a compound of the invention. Those skilled in the art will recognize that dosage forms can be modified to contain both a compound of formula I and a dopaminergic agent. The scope of the invention in its pharmaceutical composition aspect is not to be limited by the examples provided.

PHARMACEUTICAL DOSAGE FROM EXAMPLES

EXAMPLE A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process of preparing a compound of formula II

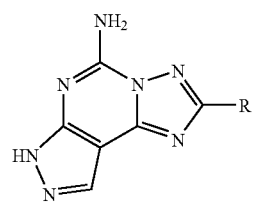

wherein R is $R^1$-furanyl, $R^1$-thienyl, $R^1$-pyridyl, $R^1$-pyridyl N-oxide, $R^1$-oxazolyl, $R^{10}$-phenyl, $R^1$-pyrrolyl or $C_4$–$C_6$ cycloalkenyl;

$R^1$ is 1 to 3 substituents independently selected from hydrogen, $C_1$–$C_6$-alkyl, —$CF_3$, halogen, —$NO_2$, $NR^{12}R^{13}$, $C_1$–$C_6$ alkoxy, $C_1$–$C_6$ alkylthio, $C_1$–$C_6$ alkylsulfinyl, and $C_1$–$C_6$ alkylsulfonyl;

$R^{10}$ is 1 to 5 substituents independently selected from the group consisting of hydrogen, halogen, $C_1$–$C_6$ alkyl, hydroxy, $C_1$–$C_6$ alkoxy, —CN, —$NH_2$, $C_1$–$C_6$alkylamino, di-(($C_1$–$C_6$)alkyl)amino, —$CF_3$, —$OCF_3$ and —$S(O)_{0-2}$($C_1$–$C_6$)alkyl;

$R^{12}$ is H or $C_1$–$C_6$ alkyl; and $R^{13}$ is ($C_1$–$C_6$)alkyl-C(O)— or ($C_1$–$C_6$)alkyl-$SO_2$—; comprising (1) treating 2-amino-4,6-dihydroxypyrimidine

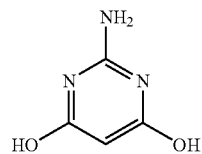

VI with POCl$_3$ in dimethylformamide to obtain 2-amino-4,6-dichloropyrimidine-5-carboxaldehyde

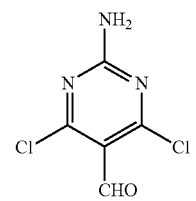

VII (2) treating carboxaldehyde VII with a hydrazide of the formula H$_2$N—NH—C(O)—R, wherein R is as defined above, to obtain

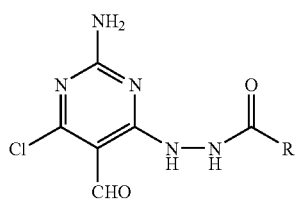

VIII (3) treating the intermediate of formula VIII with hydrazine hydrate to form a pyrazolo ring, thus obtaining the intermediate of formula IX

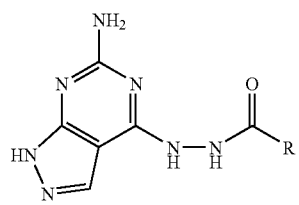

IX (4) forming the desired compound of formula II by dehydrative rearrangement.

2. A process for preparing a compound of the formula II

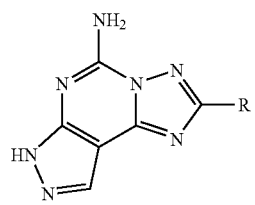

II wherein R is R$^1$-furanyl, R$^1$-thienyl, R$^1$-pyridyl, R$^1$-pyridyl N-oxide, R$^1$-oxazolyl, R$^{10}$-phenyl, R$^1$-pyrrolyl or C$_4$–C$_6$ cycloalkenyl;

R$^1$ is 1 to 3 substituents independently selected from hydrogen, C$_1$–C$_6$-alkyl, —CF$_3$, halogen, —NO$_2$, —NR$^{12}$R$^{13}$, C$_1$–C$_6$ alkoxy, C$_1$–C$_6$ alkylthio, C$_1$–C$_6$ alkylsulfinyl, and C$_1$–C$_6$ alkylsulfonyl;

R$^{10}$ is 1 to 5 substituents independently selected from the group consisting of hydrogen, halogen, C$_1$–C$_6$ alkyl, hydroxy, C$_1$–C$_6$ alkoxy, —ON, —N H$_2$, C$_1$–C$_6$alkylamino, di-((C$_1$–C$_6$)alkyl)amino, —CF$_3$, —OCF$_3$ and —S(O)$_{0-2}$(C$_1$–C$_6$)alkyl;

R$^{12}$ is H or C$_1$–C$_6$ alkyl; and

R$^{13}$ is (C$_1$–C$_6$)alkyl-C(O)— or (C$_1$–C$_6$)alkyl-S$_2$—; comprising converting a compound of formula IX

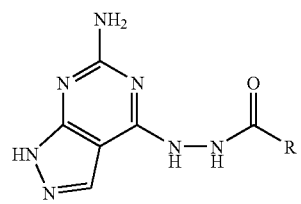

IX into the desired compound of formula II by dehydrative rearrangement.

3. A process for preparing a compound of formula IIIa

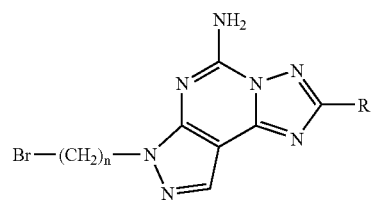

IIIa wherein R is R$^1$-furanyl, R$^1$-thienyl, R$^1$-pyridyl, R$^1$-pyridyl N-oxide, R$^1$-oxazolyl, R$^{10}$-phenyl, R$^1$-pyrrolyl or C$_4$–C$_6$ cycloalkenyl;

R$^1$ is 1 to 3 substituents independently selected from hydrogen, C$_1$–C$_6$-alkyl, —CF$_3$, halogen, —NO$_2$, —NR$^{12}$R$^{13}$, C$_1$–C$_6$ alkoxy, C$_1$–C$_6$ alkylthio, C$_1$–C$_6$ alkylsulfinyl, and C$_1$–C$_6$ alkylsulfonyl;

R$^{10}$ is 1 to 5 substituents independently selected from the group consisting of hydrogen, halogen, C$_1$–C$_6$ alkyl, hydroxy, C$_1$–C$_6$ alkoxy, —ON, —NH$_2$, C$_1$–C$_6$alkylamino, di-((C$_1$–C$_6$)alkyl)amino, —CF$_3$, —OCF$_3$ and —S(O)$_{0-2}$(C$_1$–C$_6$)alkyl;

R$^{12}$ is H or C$_1$–C$_6$ alkyl; and

R$^{13}$ is (C$_1$–C$_6$)alkyl-C(O)— or (C$_1$–C$_6$)alkyl-SO$_2$—; comprising (1) treating a chloride of formula VIII

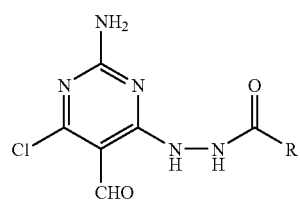

VIII with a hydroxyalkyl hydrazine of the formula HO—(CH$_2$)$_r$—NHNH$_2$, wherein r is 2–6, to obtain

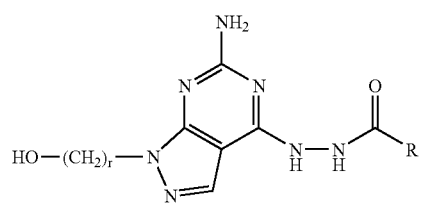
X
(2) cyclizing the intermediate of formula X by dehydrative rearrangement to obtain the tricyclic intermediate of formula XI
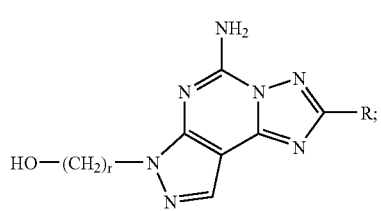
XI
(3) converting the hydroxy compound of formula XI to the bromide of formula IIIa.
* * * * *

UNITED STATES PATENT AND TRADEMARK OFFICE
CERTIFICATE OF CORRECTION

PATENT NO. : 7,067,655 B2 Page 1 of 1
APPLICATION NO. : 10/912834
DATED : June 27, 2006
INVENTOR(S) : Bernard R. Neustadt It is certified that error appears in the above-identified patent and that said Letters Patent is hereby corrected as shown below:

Claim 2, col. 94, line 3: Please correct "-ON" to --CN--.
Claim 3, col. 94, line 47: Please correct "-ON" to --CN--.

Signed and Sealed this

Fifteenth Day of April, 2008

JON W. DUDAS
*Director of the United States Patent and Trademark Office*